US008153385B2

(12) United States Patent
Yamauchi et al.

(10) Patent No.: US 8,153,385 B2
(45) Date of Patent: Apr. 10, 2012

(54) TARGET PROTEIN AND TARGET GENE IN DRUG DESIGNING AND SCREENING METHOD

(75) Inventors: Tadakazu Yamauchi, Gotenba (JP); Hideaki Sueoka, Osaka (JP); Kouichi Tsuchiya, Tokyo (JP); Katsuhisa Murayama, Osaka (JP); Kazuo Komiya, Takarazuka (JP); Morikazu Kito, Kawasaki (JP); Takeshi Tsutsumi, Osaka (JP); Yuko Isono, Yokohama (JP); Motoi Tobita, Kokubunji (JP); Yorimasa Suwa, Hino (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 1197 days.

(21) Appl. No.: 11/577,350

(22) PCT Filed: Oct. 18, 2005

(86) PCT No.: PCT/JP2005/019457
§ 371 (c)(1),
(2), (4) Date: Oct. 30, 2007

(87) PCT Pub. No.: WO2006/043691
PCT Pub. Date: Apr. 27, 2006

(65) Prior Publication Data
US 2010/0136524 A1 Jun. 3, 2010

(30) Foreign Application Priority Data

Oct. 18, 2004 (JP) .................................. 2004-303432
Mar. 25, 2005 (JP) .................................. 2005-089609

(51) Int. Cl.
G01N 33/53 (2006.01)
(52) U.S. Cl. ...................................................... 435/7.2
(58) Field of Classification Search .................... None
See application file for complete search history.

(56) References Cited

U.S. PATENT DOCUMENTS

| 3,878,217 A | 4/1975 | Carr et al. | |
|---|---|---|---|
| 2003/0181406 A1* | 9/2003 | Schetter et al. | 514/44 |
| 2004/0115726 A1 | 6/2004 | Nagashima et al. | |

FOREIGN PATENT DOCUMENTS

| JP | 48-85578 A | 11/1993 |
|---|---|---|
| JP | 2004-509406 A | 3/2004 |
| WO | WO 01/30971 A2 | 5/2001 |

OTHER PUBLICATIONS

Goldberg et al. (1996) Journal of Clinical Pharmacology 36: 1154-1160.*
Zhang et al. (1993) J. Pharm. Pharmacoloyg 45: 63-66.*
Drews, *Science*, 287: 1960-1964 (Mar. 17, 2000).
Frantz et al., *Nature Reviews*, 2: 95-96 (Feb. 2003).
Fujii et al., *Chem-Bio Informatics Journal*, 1(1): 18-22 (2001).
Hopkins et al., *Nature Reviews*, 1: 727-730 (Sep. 2002).
Liu et al., *Biochemical and Biophysical Research Communications*, 293: 1396-1404 (2002).
Ota et al., *Nature Genetics*, 36(1): 40-45 (Jan. 2004).

* cited by examiner

*Primary Examiner* — Michael Pak
(74) *Attorney, Agent, or Firm* — Leydig, Voit & Mayer, Ltd.

(57) ABSTRACT

The present invention provides a novel target protein and a gene for drug discovery, and a means that enables development of a novel pharmaceutical agent by using the same. More particularly, the present invention provides CARP and genes thereof; screening methods for drugs (e.g., antiallergic drugs); a regulator of diseases (e.g., allergic diseases); a drug derivative production method; a complex comprising a drug and CARP, and a production method thereof; kits comprising a drug or a salt thereof; determination methods for the onset or risk of onset of a specified disease, determination methods for susceptibility to a drug, and determination kits used for said methods, and the like.

8 Claims, 2 Drawing Sheets

SEQUENCE LISTING

<160> NUMBER OF SEQ ID NOS: 2

<210> SEQ ID NO 1
<211> LENGTH: 2381
<212> TYPE: DNA
<213> ORGANISM: Homo sapiens

<400> SEQUENCE: 1

| | | | | | |
|---|---|---|---|---|---|
| aagtggcacc | agcacttccg | gtacggaaaa | ctcgctgctg | ccccaacctg | gcttgacagg | 60 |
| cttggtctct | gcaagtggct | ctcagcccct | tcttctttcc | tgcctcacct | tccaattcgt | 120 |
| ttgccgccgc | cgtcccgcag | ctgctgtttc | cggagttgcc | ccttccccat | gttccggggc | 180 |
| aggagtccgc | aaagcgaaga | tccgcccgcc | ggttccccat | catgtccgaa | ctgactaaag | 240 |
| agctgatgga | gctggtgtgg | ggcaccaaga | gcagcccccgg | tctctcggac | accattttct | 300 |
| gccgctggac | gcaagggttt | gtgtttagtg | aatcagaggg | atctgcatta | gaacagtttg | 360 |
| aaggtggccc | ctgtgctgtt | attgcacctg | ttcaggcatt | tcttttgaag | aagctcctgt | 420 |
| tttcttcgga | gaagtcttct | tggcgggatt | gttcagagga | agagcagaag | gaactccttt | 480 |
| gtcataccct | tgtgtgatatt | ttagaaagtg | cttgttgtga | ccactctgga | tcatactgct | 540 |
| tggtttcatg | gttaagagga | aagacaactg | aggaaactgc | tagtatttct | gggagtcctg | 600 |
| cagagtctag | ttgccaagtg | gaacattctt | ctgccttggc | tgtcgaagag | cttggctttg | 660 |
| agcgatttca | tgcattaatt | caaaaaagat | cgttcagaag | tttaccagaa | ttaaaagatg | 720 |
| ctgtcttgga | ccagtattca | atgtggggaa | ataaatttgg | agtattgctt | tttctgtatt | 780 |
| ctgtattact | gacaaagggc | attgaaaaca | taaaaaacga | aattgaagat | gcaagtgaac | 840 |
| ccttgataga | tcctgtatat | ggacatggca | gccaaagttt | aattaatctc | ctgctgacgg | 900 |
| gacatgctgt | ttctaatgta | tgggatggtg | atagagagtg | ctcaggaatg | aaacttcttg | 960 |
| gtatacatga | acaagcagca | gtaggatttt | taacactaat | ggaagcttta | agatactgta | 1020 |
| aggttggttc | ttacttgaaa | tctccaaaat | tccctatttg | gattgttggc | agtgagactc | 1080 |
| acctcaccgt | atttttttgcc | aaggatatgg | ctttagttgc | ccctgaagct | ccttcagaac | 1140 |
| aagccagaag | agttttttcaa | acctacgacc | cagaagataa | tggattcata | cccgattcac | 1200 |
| ttctggaaga | tgtgatgaaa | gcattggacc | ttgtttcaga | tcctgaatat | ataaatctca | 1260 |
| tgaagaataa | attagatcca | gaaggattag | gaatcatatt | attgggccca | tttcttcaag | 1320 |
| aattttttcc | tgatcagggc | tccagtggtc | cagaatcttt | tactgtctac | cactacaatg | 1380 |
| gattgaagca | gtcaaattat | aatgaaaagg | tcatgtacgt | agaagggact | gcagttgtga | 1440 |
| tgggttttga | agatcccatg | ctacagacag | atgacactcc | tattaaacgc | tgtctgcaaa | 1500 |
| ccaaatggcc | atacattgag | ttactctgga | ccacagatcg | ctctccttca | ctaaattaat | 1560 |
| ttgtctaagt | atttataagg | aagatcttaa | taacagatgt | tgaaagaagg | agtcaagact | 1620 |
| ggcaattggc | tggattaagc | taaacactgg | tatcactgat | taactgtaaa | taacaattaa | 1680 |
| aaacacattt | tcagtgttta | tgatatgttt | aaattatttg | tcctaaagct | ttatgttaaa | 1740 |
| gattatccta | ttttacccct | tcgtgtgaaa | tttactagca | aaattaagct | ttcatcaaag | 1800 |
| ttcatcactt | ttgcattcag | atacttggtc | atttacttac | caaattacaa | acgcaatact | 1860 |
| acagcatttg | tatattaagt | atcacagtta | ctattgataa | actacttttg | ggttttattt | 1920 |
| cattgaggca | cttttttttat | tgtttgaatg | attccggctt | gtaatatatc | agcctctaca | 1980 |
| atgaaatgca | gaagagttca | ttttttctaag | atctgttttt | cattagaaat | attgacaaat | 2040 |

-continued

```
aacacattgt caacctggat cctttgacaa tttacttaac tctggcatgt tcacaaaaag    2100
tagaaactct aagagaccat taccatttat tcacagatgt atagggggatg tattctaaaa    2160 actgacagaa aagagaatct gatagtcaac actgttaact tttactgtgt aattgccaaa    2220 tacactttc caaatttgtc ccaacagccc tgtaagccag cttcttcta tatttataaa     2280 cacgataaat gcatgagaag atctgttatt acattagtat attacgttat ttattatgat   2340
cctagttgat ggcctaaata aacaccttt tctttaactg t                       2381
```

<210> SEQ ID NO 2
<211> LENGTH: 445
<212> TYPE: PRT
<213> ORGANISM: Homo sapiens

<400> SEQUENCE: 2

```
Met Ser Glu Leu Thr Lys Glu Leu Met Glu Leu Val Trp Gly Thr Lys
1               5                   10                  15

Ser Ser Pro Gly Leu Ser Asp Thr Ile Phe Cys Arg Trp Thr Gln Gly
                20                  25                  30

Phe Val Phe Ser Glu Ser Glu Gly Ser Ala Leu Glu Gln Phe Glu Gly
            35                  40                  45

Gly Pro Cys Ala Val Ile Ala Pro Val Gln Ala Phe Leu Leu Lys Lys
        50                  55                  60

Leu Leu Phe Ser Ser Glu Lys Ser Ser Trp Arg Asp Cys Ser Glu Glu
65                  70                  75                  80

Glu Gln Lys Glu Leu Leu Cys His Thr Leu Cys Asp Ile Leu Glu Ser
                85                  90                  95

Ala Cys Cys Asp His Ser Gly Ser Tyr Cys Leu Val Ser Trp Leu Arg
            100                 105                 110

Gly Lys Thr Thr Glu Glu Thr Ala Ser Ile Ser Gly Ser Pro Ala Glu
        115                 120                 125

Ser Ser Cys Gln Val Glu His Ser Ser Ala Leu Ala Val Glu Glu Leu
130                 135                 140

Gly Phe Glu Arg Phe His Ala Leu Ile Gln Lys Arg Ser Phe Arg Ser
145                 150                 155                 160

Leu Pro Glu Leu Lys Asp Ala Val Leu Asp Gln Tyr Ser Met Trp Gly
                165                 170                 175

Asn Lys Phe Gly Val Leu Leu Phe Leu Tyr Ser Val Leu Leu Thr Lys
            180                 185                 190

Gly Ile Glu Asn Ile Lys Asn Glu Ile Glu Asp Ala Ser Glu Pro Leu
        195                 200                 205

Ile Asp Pro Val Tyr Gly His Gly Ser Gln Ser Leu Ile Asn Leu Leu
    210                 215                 220

Leu Thr Gly His Ala Val Ser Asn Val Trp Asp Gly Asp Arg Glu Cys
225                 230                 235                 240

Ser Gly Met Lys Leu Leu Gly Ile His Glu Gln Ala Ala Val Gly Phe
                245                 250                 255

Leu Thr Leu Met Glu Ala Leu Arg Tyr Cys Lys Val Gly Ser Tyr Leu
            260                 265                 270

Lys Ser Pro Lys Phe Pro Ile Trp Ile Val Gly Ser Glu Thr His Leu
        275                 280                 285
```

-continued

```
Thr Val Phe Phe Ala Lys Asp Met Ala Leu Val Ala Pro Glu Ala Pro
    290                 295                 300

Ser Glu Gln Ala Arg Arg Val Phe Gln Thr Tyr Asp Pro Glu Asp Asn
305                 310                 315                 320

Gly Phe Ile Pro Asp Ser Leu Leu Glu Asp Val Met Lys Ala Leu Asp
                325                 330                 335

Leu Val Ser Asp Pro Glu Tyr Ile Asn Leu Met Lys Asn Lys Leu Asp
                340                 345                 350

Pro Glu Gly Leu Gly Ile Ile Leu Leu Gly Pro Phe Leu Gln Glu Phe
            355                 360                 365

Phe Pro Asp Gln Gly Ser Ser Gly Pro Glu Ser Phe Thr Val Tyr His
    370                 375                 380

Tyr Asn Gly Leu Lys Gln Ser Asn Tyr Asn Glu Lys Val Met Tyr Val
385                 390                 395                 400

Glu Gly Thr Ala Val Val Met Gly Phe Glu Asp Pro Met Leu Gln Thr
                405                 410                 415

Asp Asp Thr Pro Ile Lys Arg Cys Leu Gln Thr Lys Trp Pro Tyr Ile
                420                 425                 430

Glu Leu Leu Trp Thr Thr Asp Arg Ser Pro Ser Leu Asn
            435                 440                 445
```

TARGET PROTEIN AND TARGET GENE IN DRUG DESIGNING AND SCREENING METHOD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,297 bytes ASCII (Text) file named "701551SequenceListing.txt," created Apr. 16, 2007.

TECHNICAL FIELD

The present invention relates to target proteins and target genes for the development of drugs such as an antiallergic drug, an antiarrhythmic drug etc.; a method for screening for drugs such as an antiallergic drug, an antiarrhythmic drug etc. and a substance obtained by the screening method; a modulator of pharmacological actions of allergic condition, arrhythmia etc.; a derivative of a drug and a method of producing the derivative; and a complex comprising a drug and a target protein thereof and a method of producing the complex, and the like.

PRIOR ART

Both astemizole and terfenadine are drugs launched in the market as anti-histamine agents that are persistently effective and unlikely to cause sleepiness, for the treatment of allergic diseases such as allergic conjunctivitis, allergic rhinitis (including pollinosis) and bronchial asthma. However, their manufacturers withdrew from the market since both drugs cause liver dysfunction, and also since increases in the plasma concentrations of the unmetabolized compounds due to drug-drug interactions cause QT prolongation on electrocardiogram leading to serious arrhythmias as an adverse drug reaction.

Although the mechanism for the pharmacological effects of both drugs is known to be based mainly on the antagonization of histamine H1 receptors, the mechanism for the suppression of release of chemical mediators, which is thought to be the cause of the persistency of the pharmacological effects remains unclear. Their adverse drug reactions are attributable mainly to the inhibition of hERG channels (potential-dependent K channels), but not all of them have been elucidated. Furthermore, much remains unknown about the mechanism for the allergic diseases per se, which have recently been posing a social problem.

In recent years, on the other, the genome sequences of a variety of organisms have been elucidated and analyzed at the global level. For the human genome, in particular, a worldwide cooperative research project was implemented, and completion of analysis of all sequences thereof was announced in April 2003. Since the entire genome sequences have bee elucidated, it is becoming possible to analyze complex biological phenomena in the context of the functions and control of all genes, or networks of gene-gene, protein-protein, cell-cell, and individual-individual interactions. The genome information thus obtained has been significantly revolutionizing a number of industries, including drug development, as well as importance in academic sectors.

For example, it has been reported that there are about 480 kinds of target proteins for drugs having been in common use to date, and that these target proteins are limited to membrane receptors, enzymes, ion channels, or nuclear receptors and the like (J. Drews, Science, 287, 1960-1964, 2000). Meanwhile, target protein search based on genome information has discovered an extremely large number of target proteins, including novel proteins not covered in the conventional range of target proteins one after another, which are estimated to total about 1,500 kinds (A.L. Hopkins & C.R. Groom, Nature Reviews; Drug Discovery, 1, 727-730, 2002).

However, despite the fact that the research and development expenditures spent by pharmaceutical companies are increasing due to infrastructuring costs for coping with vast amounts of data like genome information and rises in clinical developmental costs, the number of new drugs approved is tending to decrease on the contrary (Nature Reviews; Drug Discovery, February, 2003). This shows that the above-described genome information is actually not efficiently utilized.

As a means for overcoming these circumstances, Nagashima et al. invented "Method, System, Apparatus, and Device for Discovering and Preparing Chemical Compounds for Medical and Other Uses" and filed a patent application for that invention (National Publication of Translated Version No. 2004-509406).

Disclosed in that patent application are methods, systems, databases, user interfaces, software, media, and services that are useful for the evaluation of compound-protein interactions, and are also useful for the utilization of the information resulting from such an evaluation intended to discover compounds in medical and other areas. Furthermore, it is intended to produce a very large pool of novel target proteins for drug discovery, novel methods for designing novel drugs, and a pool of small substances for therapeutic purposes that are virtually synthesized as having been inconceivable in the past.

Specifically, disclosed in that patent application were a method of identifying a protein or partial protein that is appropriate as a novel drug discovery target, which comprises the following steps:
(i) a step for selecting a plurality of proteins or partial proteins showing desired affinity and specificity for a selected target compound;
(ii) a step for identifying the structure and function of the protein or the partial protein; and
(iii) a step for selecting a single protein or single partial protein having a desired function, and a method of discovering a drug, which comprises the following steps:
(i) a step for investigating the chemical structure of the target compound selected using the above-described method; and
(ii) a step for chemically modifying the structure of the selected target compound to optimize the affinity and specificity of the modified compound for the protein or the partial protein, which is appropriate as a novel drug target.

Furthermore, feature of the method disclosed in that patent application resides in that the selected target compound is a compound approved for medical use.

Conventional drugs that have been used to date include many drugs for which target proteins are unknown, or for which target proteins are known but not all of whose pharmacological effects and adverse effects can be explained by mechanisms mediated by the proteins.

Typically, aspirin, one of the drugs that have longest been used, may be mentioned. When aspirin was launched in the market for the first time more than 100 years ago, the mechanism for its anti-inflammatory action was unclear. About 70 years later, aspirin was found to have cyclooxygenase (COX) inhibitory action. Still 20 years later, it was demonstrated that COX occurred in two subtypes: COX-1 and COX-2, that the primary pharmacological effect of aspirin was based on COX-2 inhibition, and that COX-1 inhibitory action was the cause of adverse effects such as gastrointestinal disorders. However, not all the target proteins for aspirin have been elucidated. In recent years, aspirin has been shown to exhibit anticancer action and antidementic action in clinical settings, but these pharmacological effects cannot be explained by COX inhibition. On the other, recent years have seen many papers reporting that aspirin acts on transcription factors such as IKKβ and on nuclear receptors such as PPAR-γ, but the association of these and the various pharmacological effects of aspirin remains unclear.

For these reasons, elucidating target proteins for traditionally used drugs can be said to be a very effective approach to discovering novel target proteins for drug discovery.

Hirayama, one of the inventors of the above-described published patent, and others generated a database integrating the structural and physical property data on about 1,500 kinds of drugs commercially available in Japan, and found that existing pharmaceutical compounds share structural features (Chem-Bio Informatics Journal, 1, 18-22, 2001). Drugs that have been commonly used to date can be described as excellent in that they have cleared the issues of localization in the body and safety in their developmental processes. Searching novel target protein with these existing drugs as probes, and devising novel development candidate compounds on the basis of their structures is thought to be a highly reasonable and efficient approach.

A second problem arises concerning how to make use of the genome information during the search for novel target proteins. Solely determining the genome sequence is not sufficient to ensure the elucidation of the functions of all genes and the discovery of target proteins for drug discovery. It is estimated that in humans, about 30,000 to 40,000 kinds of genes are present; taking into consideration variants from alternative splicing, there are reportedly more than 100,000 kinds of mRNA. It is important, therefore, that out of the vast amount of new genes revealed from the genome sequence, those having useful functions in industrial applications, including drug development, should be efficiently selected and identified.

In the genome sequences of eukaryotic organisms, each gene is divided into a plurality of exons by introns in many cases; therefore, it is impossible to accurately predict the structure of the protein encoded by the gene solely from the sequence information on the gene. In contrast, for a cDNA prepared from intron-excluded mRNA, information on the amino acid sequence of protein is obtained as information on a single continuous sequence, enabling easy determination of the primary structure thereof.

In particular, analyzing a full-length cDNA enables the identification of the mRNA transcription initiation point on the genome sequence based on the 5'-terminal sequence of the cDNA, and also enables analysis of the stability of mRNA contained in the sequence and of factors involved in expression control in the translation stage. Also, because the ATG codon, which serves as the translation initiation point, is present on the 5' side, translation into protein in the right frame can be achieved. Therefore, by using an appropriate gene expression system, it is also possible to mass-produce the protein encoded by the cDNA, and to express the protein and analyze the biological activity thereof. Hence, it is considered that by performing an analysis using a protein expressed from full-length cDNA, important information that could not be obtained solely by genome sequence analysis is obtained, and that it is possible to discover novel target protein for drug discovery that do not lie in the conventional category of target protein for drug discovery.

DISCLOSURE OF THE INVENTION

The objects of the present invention are to provide target proteins and genes for drug discovery, and various means that enable the development of the novel drug using the same and the like.

The present inventors diligently investigated new target proteins for drug discovery that can be useful for the development of new drugs, by analyzing interactions between human proteins and compounds that have been used as drugs by the SEC/MS method, and found that CARP can serve as a target protein for drug discovery, for example, an anti-allergic drug, anti-arrhythmic drug and the like. The present inventors conducted further investigations based on this finding, hypothesized that substances that regulate the expression or function of the CARP gene can be useful as drugs, and that drugs, for example, anti-allergic drugs and anti-arrhythmic drugs, can be developed by screening substances that regulate the expression or function of the CARP gene, or by derivatizing drugs so that the expression or function of the CARP gene can be regulated, and developed the present invention.

Accordingly, the present invention provides the following.

[1] A compound of any of the compounds represented by the following formulas (I)-(III), which has a CARP-binding ability, or a salt thereof:

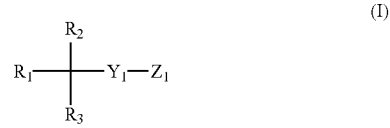

(I)

wherein $R_1$ is a hydrogen atom or hydroxy,
$R_2$ and $R_3$ are each independently phenyl or phenylalkyl having 7 to 11 carbon atoms, which is optionally substituted by 1 to 3 substituents selected from the group consisting of halogen, cyano, hydroxy and amino, and
$Y_1$ is any of the groups represented by the following formulas:

$Z_1$ is a hydrogen atom, or alkyl having 1 to 7 carbon atoms, alkenyl having 2 to 7 carbon atoms, alkyloxy having 1 to 7 carbon atoms or alkylamino having 1 to 7 carbon atoms, each of which is optionally substituted by 1 to 3 substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms, or $R_7$, wherein $R_7$ is phenyl optionally substituted by 1 to 3 substituents selected from the group consisting of alkyl having 1 to 7 carbon atoms, alkyloxy having 1 to 7 carbon atoms, carboxylic acid, alkyloxycarbonyl having 1 to 7 carbon atoms, halogen, cyano, hydroxy and amino;

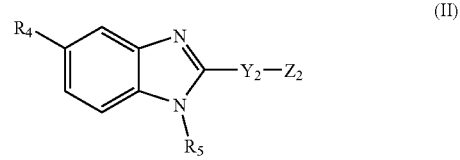

(II)

wherein R₄ is a hydrogen atom, hydroxy, or any of the groups represented by the following formulas:

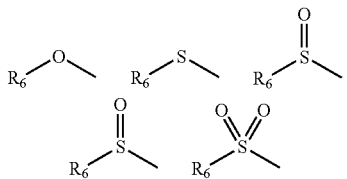

wherein R₆ is alkyl having 1 to 5 carbon atoms, cycloalkyl having 3 to 7 carbon atoms, phenyl, phenylalkyl having 7 to 11 carbon atoms or heterocycle, R₅ is a hydrogen atom, or alkyl having 1 to 5 carbon atoms, cycloalkyl having 3 to 7 carbon atoms, phenyl or phenylalkyl having 7 to 11 carbon atoms, each of which is optionally substituted by 1 or 2 substituents selected from the group consisting of a halogen atom, cyano, hydroxy and amino, Y₂ is any of the groups represented by the following formulas:
—N-A- (A is alkyl group having 1 to 3 carbon atoms)

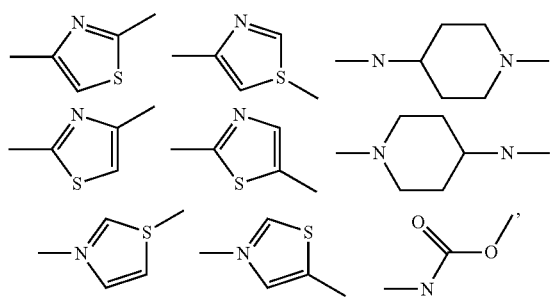

Z₂ is as defined for Z₁;

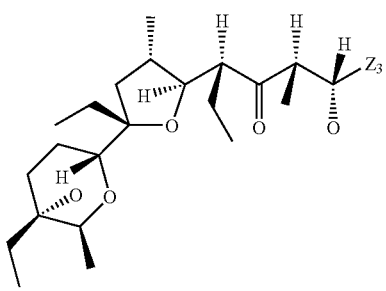

wherein Z₃ is as defined for Z₁.

[2] A drug for the treatment or prophylaxis of an allergic disease, which comprises a compound selected from the group consisting of the following formulas (I)-(III) or a salt acceptable as a pharmaceutical agent:

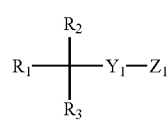

wherein R₁ is a hydrogen atom or hydroxy,

R₂ and R₃ are each independently phenyl or phenylalkyl having 7 to 11 carbon atoms, each of which is optionally substituted by 1 to 3 substituents selected from the group consisting of halogen, cyano, hydroxy and amino, Y₁ is any of the groups represented by the following formulas:

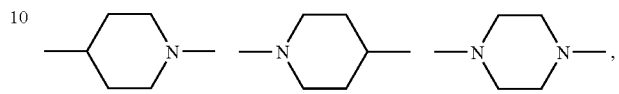

Z₁ is a hydrogen atom, or alkyl having 8 to 20 carbon atoms, alkenyl having 8 to 20 carbon atoms, alkyloxy having 8 to 20 carbon atoms or alkylamino having 8 to 20 carbon atoms, each of which is optionally substituted by 1 to 5 substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms;

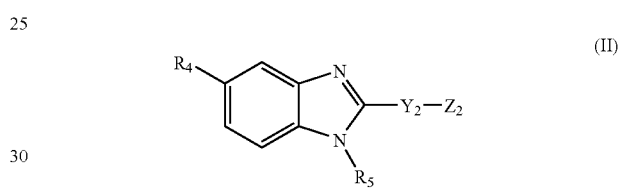

wherein R₄ is a hydrogen atom, hydroxy or any of the groups represented by the following formulas:

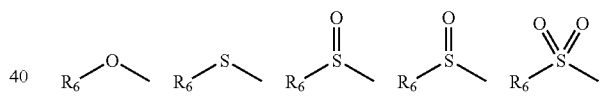

wherein R₆ is alkyl having 1 to 5 carbon atoms, cycloalkyl having 3 to 7 carbon atoms, phenyl, phenylalkyl having 7 to 11 carbon atoms or heterocycle, R₅ is a hydrogen atom, or alkyl having 1 to 5 carbon atoms, cycloalkyl having 3 to 7 carbon atoms, phenyl or phenylalkyl having 7 to 11 carbon atoms, each of which is optionally substituted by 1 or 2 substituents selected from the group consisting of a halogen atom, cyano, hydroxy and amino, Y₂ is any of the groups represented by the following formula:
—N-A- (A is alkyl group having 1 to 3 carbon atoms)

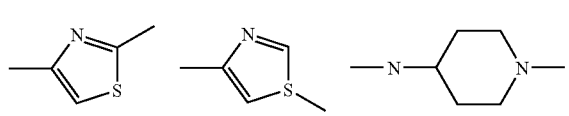

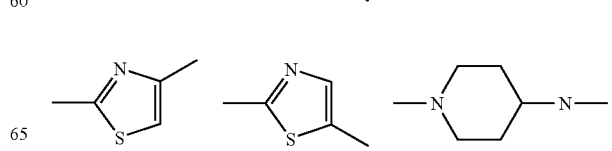

-continued

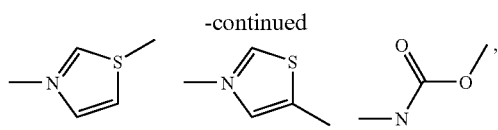

$Z_2$ is as defined for $Z_1$;

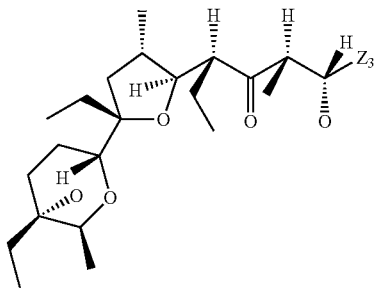

wherein $Z_3$ is a hydrogen atom, or alkyl having 1 to 7 carbon atoms, alkenyl having 2 to 7 carbon atoms, alkyloxy having 1 to 7 carbon atoms or alkylamino having 1 to 7 carbon atoms, each of which is optionally substituted by 1 to 5 substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms, or $R_8$, wherein $R_8$ is phenyl optionally substituted by 1 to 3 substituents selected from the group consisting of alkyl having 1 to 7 carbon atoms, alkyloxy having 1 to 7 carbon atoms, carboxylic acid, halogen, cyano, hydroxy and amino.

[3] A screening method for a drug, which comprises determining whether or not a test substance is capable of regulating the expression or function of the CARP gene.

[4] The method according to [3] above, wherein the drug is a substance capable of regulating allergic symptoms, a substance capable of regulating the release of a chemical mediator, or a substance capable of regulating arrhythmic symptoms;

[5] The method according to [3] above, which comprises the following steps (a)-(c):
(a) a step for bringing the test substance in contact with CARP or mutant protein thereof;
(b) a step for measuring the functional level of the protein or mutant protein thereof in the presence of the test substance, and comparing the functional level with that of the protein or mutant protein thereof in the absence of the test substance;
(c) a step for selecting a test substance that alters the functional level of the protein or mutant protein thereof on the basis of the results of the comparison in step (b) above.

[6] The method according to [3] above, which comprises the following steps (a), (b) and (c):
(a) a step for bringing the test substance and cells allowing a measurement of the expression of the CARP gene into contact with each other;
(b) a step for measuring the expression amount of the CARP gene in the cells in contact with the test substance, and comparing this expression amount with the expression amount of the CARP gene in control cells not in contact with the test substance;
(c) a step for selecting a test substance that regulates the expression amount of the CARP gene on the basis of the results of the comparison in step (b) above.

[7] The method according to [3] above, which comprises the following steps (a), (b) and (c):
(a) a step for bringing the test substance into contact with CARP or mutant protein thereof;
(b) a step for measuring the binding ability of the test substance to the protein;
(c) a step for selecting a test substance capable of binding to the protein on the basis of the results in step (b) above.

[8] The method according to [3] above, which comprises the following steps (a), (b) and (c):
(a) a step for bringing the test substance and a CARP-binding substance into contact with CARP or mutant protein thereof;
(b) a step for measuring the binding level of the binding substance to the protein in the presence of the test substance, and comparing this binding level with the binding level of the binding substance to the protein in the absence of the test substance;
(c) a step for selecting a test substance that alters the binding level of the binding substance to the protein on the basis of the results of the comparison in step (b) above.

[9] The method according to [8] above, wherein the CARP-binding substance is astemizole or terfenadine, or metabolite thereof, or α,α-diphenyl-4-piperidinomethanol, hydroxyzine, desmethylastemizole, 2-amino-1-benzyl-benzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

[10] A screening method for a substance capable of regulating a function associated with the CARP gene, which comprises determining whether or not a test substance is capable of regulating the binding ability of a CARP target drug to CARP or mutant protein thereof.

[11] The method according to [10] above, wherein the CARP target drug is astemizole or terfenadine, or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

[12] The method according to [10] above, which comprises the following steps (a) to (c):
(a) a step for bringing the test substance and the CARP target drug into contact with CARP or mutant protein thereof;
(b) a step for measuring the binding level of the CARP target drug to the protein in the presence of the test substance, and comparing this binding level with the binding level of the CARP target drug to the protein in the absence of the test substance;
(c) a step for selecting a test substance that alters the binding level of the CARP target drug to the protein on the basis of the results of the comparison in step (b) above.

[13] A substance obtained by the method according to any of [3] to [12] above.

[14] A regulator of a pharmacological action, which comprises a substance obtained by the method according to any of [3] to [12] above.

[15] A regulator of a pharmacological action, which comprises a substance that regulates the expression or function of the CARP gene.

[16] The regulator according to [15] above, which is a regulator of allergic symptoms, a regulator of chemical mediator release, a regulator of arrhythmic symptoms, or a regulator of alopecic symptoms;

[17] The regulator according to [15] above, which is a regulator of an action associated with a CARP target drug.

[18] The regulator according to [15] above, wherein the substance that regulates the expression or function of the CARP gene is a substance that suppresses the expression or function of the CARP gene of (i) or (ii) below:

(i) a nucleic acid selected from the group consisting of a CARP antisense nucleic acid, a CARP ribozyme, a CARP decoy nucleic acid, CARP siRNA, a nucleic acid that encodes a CARP antibody and a nucleic acid that encodes a CARP dominant negative mutant, or an expression vector comprising the nucleic acid; or (ii) a protein selected from the group consisting of a CARP antibody and a CARP dominant negative mutant.

[19] A regulator of a pharmacological action, which comprises CARP or mutant protein thereof, or an expression vector comprising a nucleic acid that encodes the protein.

[20] A regulator of a function associated with the CARP gene, which comprises a CARP target drug.

[21] The regulator according to [20] above, wherein the CARP target drug is astemizole or terfenadine, or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

[22] A production method for a drug derivative, which comprises derivatizing a drug so that a function of the CARP gene can be regulated.

[23] The method according to [22] above, wherein the drug is a substance capable of regulating allergic symptoms, a substance capable of regulating the release of a chemical mediator, a substance capable of regulating arrhythmic symptoms or a substance capable of regulating alopecic symptoms.

[24] The method according to [22] above, wherein the drug is astemizole or terfenadine, or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

[25] A production method for a derivative of a substance capable of regulating a function associated with the CARP gene, which comprises derivatizing a drug so that the binding ability thereof to CARP or mutant protein thereof can be regulated.

[26] The method according to [25] above, wherein the drug is astemizole or terfenadine, or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

[27] A substance obtained by the method according to any of [22] to [26] above.

[28] A regulator of a pharmacological action, which comprises a substance obtained by the method according to any of [22] to [26] above.

[29] A complex comprising a drug and CARP or mutant protein thereof.

[30] A production method for a complex comprising a drug and CARP or mutant protein thereof, which comprises bringing the drug and CARP or mutant protein thereof into contact with each other.

[31] A kit comprising the following (i) and (ii):
(i) a drug or a salt thereof;
(ii) CARP or mutant protein thereof, a nucleic acid that encodes the protein, an expression vector comprising the nucleic acid, cells allowing a measurement of the expression of the CARP gene, or an expression vector comprising the transcription regulatory region of the CARP gene and a reporter gene functionally linked to the region.

BEST MODE FOR EMBODIMENT OF THE INVENTION

1. CARP and Genes Thereof

Figure 1:
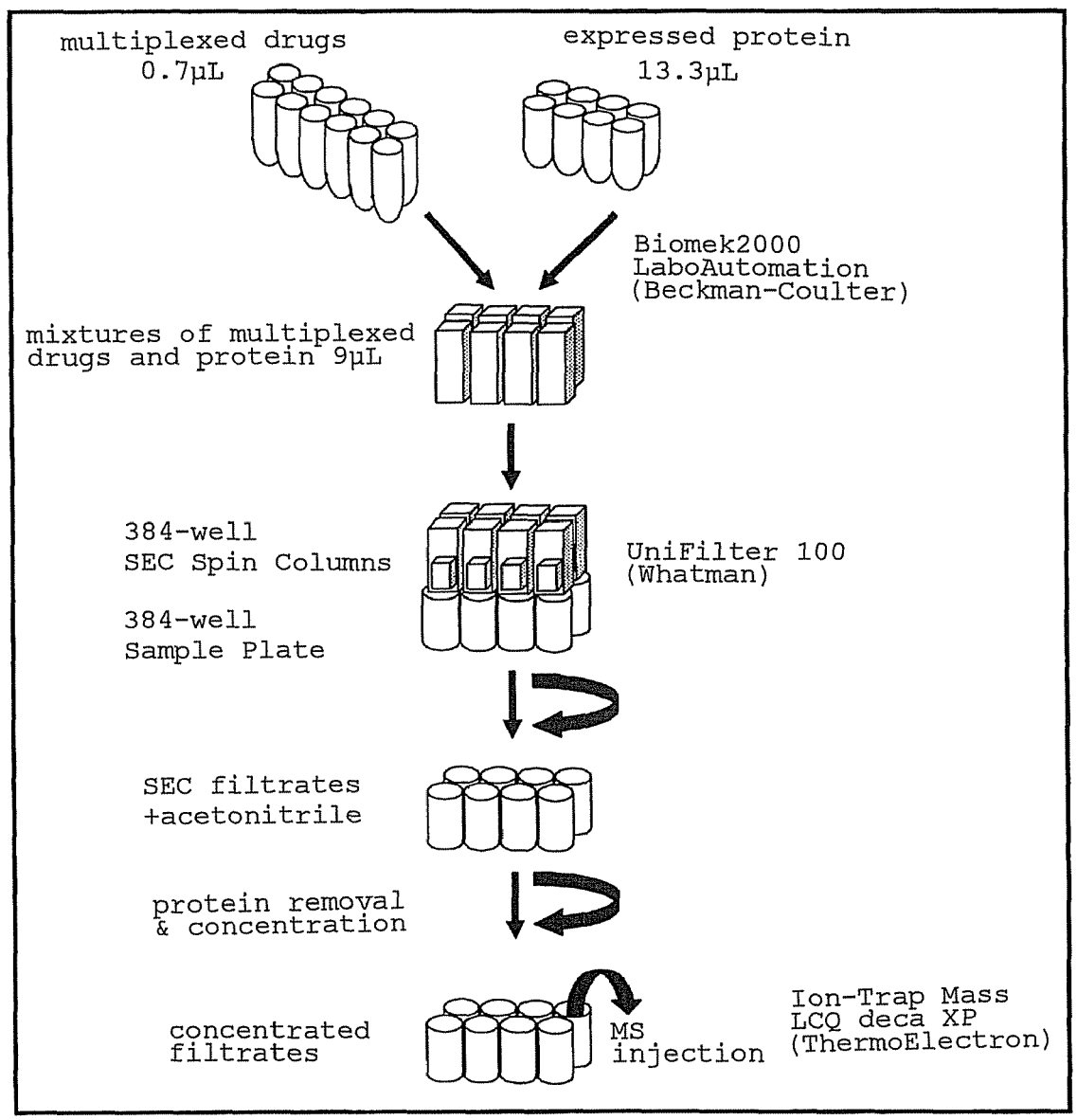
FIG. 1 shows a schematic diagram showing a SEC interaction screening system using a spin column.

The present invention provides CARP and genes.

CARP (caspase recruitment domain containing protein) is a protein having a site like the caspase recruitment domain (CARD) related to apoptosis, a site like the binding motif to nuclear receptor (NR box), and a site like the EF hand capable of binding to calcium (see Liu B et al., Biochem Biophys Res Commun., 293(5), 1396-404 (2002)). CARP is a protein encoded by C10orf97 (chromosome 10 open reading frame 97) gene, and is also known by different names of brain my042 protein, normal aorta protein MSTP126 and dermal papilla derived protein 5 (DERP5). CARP is also known to be expressed in the heart, skeletal muscle, brain, lungs, kidneys, liver, spleen, large intestine, small intestine, placenta and the like. As mentioned herein, CARP is not limited to human CARP, but includes orthologues of different animal species. CARP is a protein derived from the FLJ13397 clone described in an Example below.

The CARP of the present invention can be, for example, a protein having the amino acid sequence shown by SEQ ID NO:2. The human CARP has been registered under the FLJ number (registration number in the NEDO (New Energy and Industrial Technology Development Organization) protein cDNA structural analysis project) of FLJ13397, the GenBank accession number of AK023459, and the H-Inv cDNA ID number of HIT000006733 and H-Inv locus ID number of HIX0008676 in the H-Invitational database (H-Inv DB) (see Nat. Genet. 36(1), 40-45 (2004)), and has been found by the present inventors to interact with drugs such as astemizole and terfenadine.

According to the present invention, a mutant protein of CARP is provided. The mutant protein can be, for example, a protein that consists of the amino acid sequence shown by SEQ ID NO:2 wherein one or more amino acids have been deleted, substituted, added or inserted, and that interacts with a drug.

The number of amino acids substituted, deleted, added or inserted can be any one that allows the retention of the function, for example, about 1 to 30, preferably about 1 to 20, more preferably about 1 to 10, further more preferably about 1 to 5, most preferably 1 or 2. The site for substitution, deletion, addition or insertion of an amino acid can be any site that allows the retention of the function, for example, a site other than functionally important domains; for example, sites other than CARD-like site, NR box-like site and EF hand-like site.

Furthermore, the mutant protein provided by the present invention can be a protein which consists of, for example, an amino acid sequence having a homology of about 50% or more, preferably about 70% or more, more preferably about 80% or more, further more preferably about 90% or more, most preferably about 95% or more (but excluding 100% homology), to the amino acid sequence shown by SEQ ID NO:2, and which interacts with a drug. Here, the numerical values of the above-described homology are calculated by, for example, executing the commands for the maximum matching method using the DNASIS sequence analytical software (Hitachi Software Engineering). The parameters for the calculation should be used in default settings (initial settings).

A drug with which a protein of the present invention interacts is a CARP target drug. A CARP target drug refers to a drug that exhibits a pharmacological effect or adverse drug reaction via CARP. Examples of such drugs include a substance capable of regulating an action associated with a CARP target drug (e.g., a substance capable of regulating allergic symptoms, a substance capable of regulating the release of, a chemical mediator), a substance capable of regulating a function associated with the CARP gene, and the like. The term drug is to be understood to include a pharmaceutical and a reagent.

When the CARP of the present invention or a mutant protein thereof is used, the protein may be a labeled supply or a non-labeled supply, or a mixture of a labeled supply and a non-labeled supply mixed in a specified ratio. Examples of the labeling substance include fluorescent substances such as FITC and FAM, luminescent substances such as luminol, luciferin and lucigenin, radioisotopes such as $^3$H, $^{14}$C, $^{32}$P, $^{35}$S, and $^{123}$I, affinity substances such as biotin and streptavidin, and the like.

The CARP gene of the present invention may be any gene that encodes the CARP of the present invention. For example, the CARP gene of the present invention can be a gene corresponding to a protein consisting of one of the above-described amino acid sequences. Preferably, the CARP gene of the present invention consists of the nucleotide sequence shown by SEQ ID NO:1. The CARP gene of the present invention is not limited to the above-described human genes, but includes orthologues of different animal species.

The present invention also provides a gene that consists of a nucleotide sequence that hybridizes to a sequence complementary to the nucleotide sequence shown by SEQ ID NO: 1 under stringent conditions, and that corresponds to a protein that interacts with a drug. Here, "hybridize under stringent conditions" means that a positive hybridization signal remains observable even under conditions of, for example, heating in a solution of 6×SSC, 0.5% SDS and 50% formamide at 42° C., followed by washing in a solution of 0.1×SSC and 0.5% SDS at 68° C.

The CARP of the present invention and the gene thereof are useful for the development of pharmaceuticals for various diseases, for example, a disease associated with a CARP target drug (e.g., allergic diseases, diseases for which regulation of the release of a chemical mediator is desired, arrhythmic symptoms), and a disease associated with the CARP gene, or for the development of investigational reagents for the diseases, and the like. The individual diseases are hereinafter described in detail.

(I. Diseases Associated with Carp Target Drugs)

"A disease associated with a CARP target drug" means a disease for which a CARP target drug is used or a disease corresponding to an adverse drug reaction of the drug. A disease associated with a CARP target drug can be ameliorated or exacerbated with a CARP target drug. Examples of the disease associated with a CARP target drug include allergic diseases, diseases associated with chemical mediators, arrhythmic symptoms, and other diseases.

"An action associated with a CARP target drug" means an action of the same kind as, or opposite kind to, a kind of action actually exhibited by the CARP target drug (including pharmacological actions and adverse drug reactions). That is, an action associated with a CARP target drug is an action capable of ameliorating or exacerbating "a disease associated with a CARP target drug". Hence, provided that the disease associated with a CARP target drug is an allergic disease, the action associated with a CARP target drug is allergy-inducing action or anti-allergic action. "Actions associated with CARP target drugs" will become obvious through the description of "diseases associated with CARP target drugs".

(I(a). Allergic Diseases)

Although the allergic disease is not subject to limitation, a disease classified as type I allergy is preferable. Examples of such allergic diseases include bronchial asthma, allergic conjunctivitis, allergic rhinitis, pollinosis, atopic dermatitis, urticaria, food allergy and the like. Astemizole and terfenadine are known as anti-allergic drugs. Hence, because astemizole and terfenadine are considered to be capable of exhibiting their pharmacological effects by binding to CARP to activate or inhibit the signal transduction system that cooperates with CARP, a substance capable of regulating the expression or function of the CARP gene can exhibit allergy-inducing action or anti-allergic action.

(I(b). Diseases for which Regulation of the Release of a Chemical Mediator is Desired)

A chemical mediator means a biological substance secreted from optionally chosen cells in the body, which possesses bioactivity. Examples of the chemical mediator include quaternary ammonias such as acetylcholine, amines such as histamine, serotonin, norepinephrine and dopamine, amino acids such as glutamine, GABA and glycine, peptides such as substance P, somatostatin, enkephalin and β-endorphin, cytokines such as interleukins and GM-CSF, polysaccharides such as heparin, bioactive lipids such as PAF, prostaglandin, thromboxane and leukotriene, and the like. Astemizole and terfenadine are known to exhibit their pharmacological effects by regulating the release of chemical mediators. Hence, a substance capable of regulating the expression or function of CARP is considered to be capable of regulating the release of a chemical mediator. The regulation of the release of a chemical mediator can be the promotion or suppression of the release of a chemical mediator.

A disease for which regulation of the release of a chemical mediator is desired is a disease associated with an action of one of the above-described chemical mediators; examples include immune diseases, including the above-described allergic diseases, central nervous and peripheral nervous diseases, and endocrine diseases and the like.

(I(c). Arrhythmic Symptoms)

The arrhythmic symptoms are not subject to limitation; examples include QT interval prolongation, torsades de pointes (ventricular tachycardia), extrasystole (atrial extrasystole, ventricular extrasystole), bradyarrhythmias (sick sinus syndrome, atrioventricular block), tachyarrhythmias (atrial tachycardia, atrial flutter and fibrillation, paroxysmal supraventricular tachycardia (including WPW syndrome), ventricular tachycardia, ventricular fibrillation and the like, with preference given to QT interval prolongation and torsades de pointes (ventricular tachycardia). Astemizole and terfenadine are known to possibly cause cardiovascular disorders. Hence, a substance capable of regulating the expression or function of the CARP gene is considered to be capable of inducing or preventing/treating arrhythmic symptoms.

(I(d). Other Diseases)

The disease associated with a CARP target drug can be a disease associated with astemizole or terfenadine.

A disease associated with astemizole means a disease for which astemizole is used or a disease corresponding to an adverse drug reaction of astemizole. Astemizole is known as an anti-allergic drug and the like. Examples of the disease for which astemizole is used include bronchial asthma, urticaria, eczema/dermatitis, skin pruritis, allergic rhinitis and the like. Examples of the adverse drug reaction of astemizole include death, syncope, cardiac (beat) arrest, QT interval prolongation, torsades de pointes (ventricular tachycardia), premature ventricular twitch, ventricular arrhythmias, lethargy, headache, fatigue, dizziness, sleepiness, torpor, depression, paresthesia, psychomotor disorder convulsion, dry mouth, nausea, abdominal pain, distention, diarrhea, cardiovascular disorders [QT prolongation, ventricular arrhythmias (including torsades de pointes), cardiac arrest (including death) and the like], pancytopenia and the like. As target for astemizole, histamine H1 receptor is known.

A disease associated with terfenadine means a disease for which terfenadine is used or a disease corresponding to an adverse drug reaction of terfenadine. Terfenadine is known as an anti-allergic drug and the like. Examples of the disease for which terfenadine is used include allergic rhinitis, bronchial asthma, eczema, urticaria, dermatitis, skin pruritis and the like. Examples of the adverse drug reaction of terfenadine include thrombocytopenia, ventricular fibrillation, death, cardiac arrest, hypotension, palpitation, syncope, QT interval prolongation, tachycardia, torsades de pointes (ventricular tachycardia) and the like. As target for terfenadine, histamine H1 receptor is known.

Moreover, a disease associated with a CARP protein target drug can be a disease associated with a CARP-binding compound. CARP-binding compound is, for example, α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid.

The disease associated with albendazol refers to a disease to which albendazol can be used or a disease corresponding to adverse drug reaction of albendazol. Albendazol is known as an anthelmintic agent and the like. The disease to which albendazol can be used is exemplified by a hydatid disease and the like. On the other hand, the adverse drug reaction of albendazol is exemplified by liver•bile duct disorders (liver function disorder, AST(GOT) increase, ALT(GPT) increase), pancytopenia and the like.

The disease associated with mebendazole refers to a disease to which mebendazole can be used or a disease corresponding to adverse drug reaction of mebendazole.

Mebendazole is known as an anthelmintic agent and the like. The disease to which mebendazole can be used is exemplified by trichuriasis and the like. On the other hand, the adverse drug reaction of mebendazole is exemplified by hepatopathy, anthema and the like.

The disease associated with carbendazim refers to a disease to which carbendazim can be used or a disease corresponding to adverse drug reaction of carbendazim. Carbendazim is known as an antibacterial agent, insecticide, an antifungal agent and the like. In addition, as the action of carbendazim, microtubule hypofunction and the like can be mentioned.

The disease associated with thiabendazole refers to a disease to which thiabendazole can be used or a disease corresponding to adverse drug reaction of thiabendazole. Thiabendazole is known as an antibacterial agent, insecticide, an antifungal agent and the like. In addition, as the action of thiabendazole, microtubule hypofunction and the like can be mentioned.

The disease associated with nocodazol refers to a disease to which nocodazol can be used or a disease corresponding to adverse drug reaction of nocodazol. In addition, as the action of nocodazol, microtubule formation inhibition, nucleospindle formation inhibition and the like can be mentioned.

The disease associated with lasalocid refers to a disease to which lasalocid can be used or a disease corresponding to adverse drug reaction of lasalocid. Lasalocid is a polyether ionophore antibiotic and known as an antibacterial agent, an antiprotozoal agent and the like. In addition, as the action of lasalocid, promotion or inhibition of apoptosis and the like can be mentioned.

(II. Diseases Associated with the Carp Gene)

"A disease associated with the CARP gene" refers to a disease possibly caused due to a change in a function or expression amount of the CARP gene, or a function or expression amount of a gene located downstream of the CARP gene in the signal transduction system mediated by the CARP gene (downstream gene). A functional change in the CARP gene or a downstream gene thereof can be caused by, for example, a mutation (e.g., polymorphism) of the gene. Examples of the mutation include a mutation that promotes or suppresses a function of the gene in the coding region, a mutation that promotes or suppresses the expression of the gene in the non-coding region, and the like. Examples of the change in the expression amount include increases or reductions in the expression amount. A disease associated with the CARP gene can be ameliorated or exacerbated by CARP.

"A function associated with the CARP gene" means a function of the same kind as, or opposite kind to, a kind of function actually exhibited by CARP. That is, "a function associated with the CARP gene" is a function capable of ameliorating or exacerbating "a disease associated with the CARP gene". Examples of the function associated with the CARP gene include caspase-related functions (e.g., provocation, promotion or suppression of apoptosis, induction, promotion or suppression of production of cytokines such as IL-1α, IL-1β, TNF-α and IL-6), activation or suppression of nuclear receptors (e.g., gene expression regulatory function, lipid metabolism regulatory function, cell differentiation regulatory function, cell proliferation regulatory function, immune reaction regulatory function) and the like.

In view of the fact that the CARP gene is considered to be responsible for various physiological functions in the body, quite a wide variety of diseases are likely to be associated with the CARP gene; examples include various cancers, immune diseases, inflammatory diseases, metabolic diseases, nervous system diseases, respiratory diseases, cardiovascular diseases, bone diseases, skin diseases, alopecia and the like. Other diseases possibly associated with the CARP gene include arrhythmogenic right ventricular dysplasia (familial) 6 (OMIM ID:604401) and Hansen's disease (OMIM ID:246300).

(III. Carp Target Drug)

The compounds of the formulas (I)-(III) of the present invention are explained.

The present inventors have found that the compounds of the formulas (I)-(III) has a binding ability to CARP, and can be used as a pharmaceutical agent such as antiallergic drug and the like (see the above), or CARP binding probe, affinity resin, label, CARP function regulator (see the above) and the like.

Compounds represented by the formulas (I)-(III) can be produced by applying various known synthesis methods based on the basic skeleton or the kind of substituent. For example, alkylation, acylation, amination, imination, halogenation, reduction, oxidation, condensation, cyclization and the like can be mentioned, and the reactions and methods generally used in this field can be utilized.

The compounds of the formulas (I)-(III) can be represented by the formula X-Z. More particularly, the compound of the formula (I) can be represented by $X_1$-$Z_1$($Z_{1a}$ or $Z_{1b}$), the compound of the formula (II) can be represented by $X_2$-$Z_2$ ($Z_{2a}$ or $Z_{2b}$), and the compound of the formula (III) can be represented by $X_3$-$Z_3$ ($Z_{3a}$ or $Z_{3b}$).

$X_1$-$X_3$ can be as follows:

$X_1$:

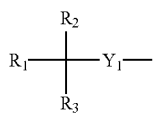

wherein $R_1$ is a hydrogen atom or hydroxy,
$R_2$ and $R_3$ are each independently phenyl or phenylalkyl having 7 to 11 carbon atoms optionally substituted by 1 to 3 substituents selected from the group consisting of halogen, cyano, hydroxy and amino,
$Y_1$ is any of the groups represented by the following formulas:

$X_2$:

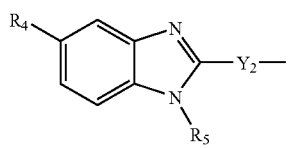

wherein $R_4$ is a hydrogen atom, hydroxy, or any of the groups represented by the following formulas:

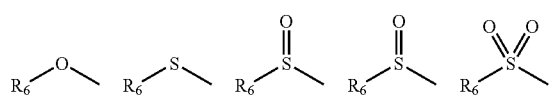

wherein $R_6$ is alkyl having 1 to 5 carbon atoms, cycloalkyl having 3 to 7 carbon atoms, phenyl, phenylalkyl having 7 to 11 carbon atoms or heterocycle, $R_5$ is a hydrogen atom, or alkyl having 1 to 5 carbon atoms, cycloalkyl having 3 to 7 carbon atoms, phenyl or phenylalkyl having 7 to 11 carbon atoms, each of which is optionally substituted by 1 or 2 substituents selected from the group consisting of a halogen atom, cyano, hydroxy and amino, $Y_2$ is any of the groups represented by the following formulas:
—N-A- (A is alkyl group having 1 to 3 carbon atoms)

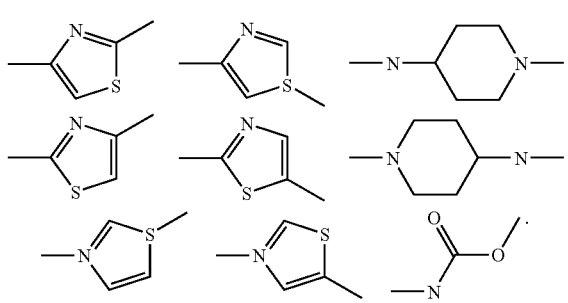

$X_3$:

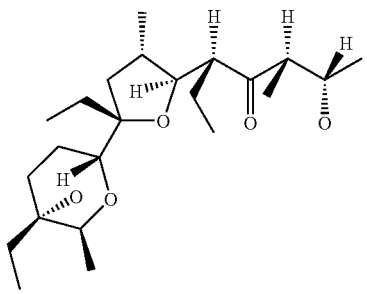

$Z_{1a}$-$Z_{3a}$ are each independently a hydrogen atom, or alkyl having 1 to 7 carbon atoms, alkenyl having 2 to 7 carbon atoms, alkyloxy having 1 to 7 carbon atoms or alkylamino having 1 to 7 carbon atoms, each of which is optionally substituted by 1 to 3 substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms, or $R_7$. As $R_7$, for example, phenyl optionally substituted by 1 to 3 substituents selected from the group consisting of alkyl having 1 to 7 carbon atoms, alkyloxy having 1 to 7 carbon atoms, carboxylic acid, alkyloxycarbonyl having 1 to 7 carbon atoms, halogen, cyano, hydroxy and amino can be mentioned.

$Z_{1b}$ and $Z_{2b}$ can be each independently a hydrogen atom, or alkyl having 8 to 20 carbon atoms, alkenyl having 8 to 20 carbon atoms, alkyloxy having 8 to 20 carbon atoms or alkylamino having 8 to 20 carbon atoms, each of which is optionally substituted by 1 to 5 (e.g., 1 to 3) substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms. $Z_{3b}$ can be, for example, a hydrogen atom, or alkyl having 1 to 7 carbon atoms, alkenyl having 2 to 7 carbon atoms, alkyloxy having 1 to 7 carbon atoms or alkylamino having 1 to 7 carbon atoms, each of which is optionally substituted by 1 to 5 (e.g., 1 to 3) substituents selected from the group consisting of halogen, cyano, hydroxy, carbonyl, amino, alkyl having 1 to 5 carbon atoms, alkyloxy having 1 to 5 carbon atoms and cycloalkyl having 3 to 7 carbon atoms, or $R_8$. As $R_8$, for example, phenyl optionally substituted by 1 to 3 substituents selected from the group consisting of alkyl having 1 to 7 carbon atoms, alkyloxy having 1 to 7 carbon atoms, carboxylic acid, halogen, cyano, hydroxy and amino can be mentioned.

The "halogen atom" is a fluorine atom, a chlorine atom, a bromine atom or an iodine atom.

As the "phenylalkyl having 7 to 11 carbon atoms", for example, benzyl, phenethyl, phenylpropyl, phenylisopropyl, phenylbutyl and the like can be mentioned.

The "alkyl having 1 to 7 carbon atoms" can be a straight chain or a branched chain and, for example, methyl, ethyl, propyl, isopropyl, butyl, isobutyl, sec-butyl, tent-butyl, pentyl, isopentyl, neopentyl, sec-pentyl, tert-pentyl, hexyl, isohexyl, 2-ethylbutyl, heptyl and the like can be mentioned.

The "alkyl having 1 to 5 carbon atoms" can be a straight chain or a branched chain and, for example, of the aforementioned alkyl, those having 1 to 5 carbon atoms can be mentioned.

The "alkyl having 8 to 20 carbon atoms" can be a straight chain or a branched chain and, for example, octyl, nonyl, decanyl, undecanyl, dodecanyl, tridecanyl, icosanyl and the like can be mentioned.

As the "alkyloxy having 1 to 7 carbon atoms", for example, methoxy, ethoxy, propyloxy, isopropyloxy, butyloxy, isobutyloxy, sec-butyloxy, tert-butyloxy, pentyloxy, isopentyloxy, neopentyloxy, sec-pentyloxy, tert-pentyloxy and the like can be mentioned.

As the "alkyloxy having 1 to 5 carbon atoms", for example, of the aforementioned alkyloxy, those having 1 to 5 carbon atoms can be mentioned.

The "alkyloxy having 8 to 20 carbon atoms" is, for example, octyloxy, nonyloxy, decanyloxy, undecanyloxy, dodecanyloxy, tridecanyloxy, icosanyloxy and the like.

As the "cycloalkyl having 3 to 7 carbon atoms", for example, cyclopropyl, cyclobutyl, cyclopentyl, cyclohexyl and cycloheptyl can be mentioned.

The "alkenyl having 2 to 7 carbon atoms" can be, for example, a straight chain or a branched chain and, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, hexenyl, heptenyl and the like can be mentioned.

The "alkenyl having 8 to 20 carbon atoms" can be a straight chain or a branched chain and, for example, octenyl, nonenyl, decenyl, undecenyl, dodecenyl, tridecenyl, icocenyl and the like can be mentioned.

The "alkylamino having 1 to 7 carbon atoms" can be amino monosubstituted by straight chain or branched chain alkyl having 1 to 7 carbon atoms, or amino disubstituted by straight chain or branched chain alkyl having 1 to 6 carbon atoms. As the amino monosubstituted by straight chain or branched chain alkyl having 1 to 7 carbon atoms, for example, N-methylamino, N-ethylamino, N-propylamino, N-isopropylamino, N-butylamino, N-isobutylamino, N-sec-butylamino, N-tert-butylamino, N-pentylamino, N-isopentylamino, N-neopentylamino, N-sec-pentylamino, N-tert-pentylamino, N-hexylamino, N-isohexylamino, N-2-ethylbutylamino, N-heptylamino and the like can be mentioned. As the amino disubstituted by straight chain or branched chain alkyl having 1 to 6 carbon atoms, for example, N,N-dimethylamino, N,N-diethylamino, N,N-dipropylamino, N,N-diisopropylamino, N-ethyl-N-methylamino, N-propyl-N-methylamino, N-isopropyl-N-methylamino, N-butyl-N-methylamino, N-isobutyl-N-methylamino, N-sec-butyl-N-methylamino, N-tert-butyl-N-methylamino, N-pentyl-N-methylamino, N-isopentyl-N-methylamino, N-neopentyl-N-methylamino, N-sec-pentyl-N-methylamino, N-tert-pentyl-N-methylamino, N-hexyl-N-methylamino, N-isohexyl-N-methylamino and the like can be mentioned.

The "alkylamino having 8 to 20 carbon atoms" can be amino monosubstituted by straight chain or branched chain alkyl having 8 to 20 carbon atoms, or amino disubstituted by straight chain or branched chain alkyl having 1 to 7 carbon atoms. As the amino monosubstituted by straight chain or branched chain alkyl having 8 to 20 carbon atoms, for example, N-octylamino, N-nonylamino, N-decanylamino, N-undecanylamino, N-dodecanylamino, N-tridecanylamino, N-icosanylamino and the like can be mentioned. As the amino disubstituted by straight chain or branched chain alkyl having 1 to 7 carbon atoms, for example, N-heptyl-N-methylamino, N-octyl-N-methylamino, N-(1,1,3,3-tetramethylbutyl)-N-methylamino, N-nonyl-N-methylamino, N-decanyl-N-methylamino, N-undecanyl-N-methylamino, N-dodecanyl-N-methylamino, N-tridecanyl-N-methylamino and the like can be mentioned.

The "alkyloxycarbonyl having 1 to 7 carbon atoms" can be carbonyl substituted by the aforementioned alkyloxy having 1 to 7 carbon atoms and, for example, methoxycarbonyl, ethoxycarbony, propyloxycarbonyl, isopropyloxycarbonyl, butyloxycarbonyl, isobutyloxycarbonyl, sec-butyloxycarbonyl, tert-butyloxycarbonyl, pentyloxycarbonyl, isopenptyloxycarbonyl, neopentyloxycarbonyl, sec-pentyloxycarbonyl, tert-pentyloxycarbonyl and the like can be mentioned.

The "heterocycle" can be a 4- to 7-membered (preferably 5- or 6-membered) monocyclic aromatic or non-aromatic heterocycle, or 4- to 13-membered condensed aromatic or non-aromatic heterocycle, containing, as a ring-constituting atom besides carbon atom, 1 to 4 (preferably 1 to 3, more preferably 1 or 2) hetero atoms selected from an oxygen atom, a sulfur atom and a nitrogen atom. As such monocyclic aromatic heterocycle, for example, furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl and the like can be mentioned. As such monocyclic non-aromatic heterocycle, for example, pyrrolidinyl, piperidinyl, morpholinyl, thiomorpholinyl, piperazinyl, hexamethyleneiminyl, oxazolidinyl, thiazolidinyl, imidazolidinyl, dioxolyl, dioxolanyl, tetrahydropyranyl, tetrahydrothiopyranyl and the like can be mentioned. As such condensed aromatic heterocycle, for example, quinolyl, isoquinolyl, quinazolyl, quinoxalyl, phthalazinyl, benzofuryl, benzothienyl, benzoxazolyl, benzothiazolyl, benzimidazolyl, indolyl, indazolyl and the like can be mentioned. As such condensed non-aromatic heterocycle, for example, dihydroquinolinyl, tetrahydroquinolinyl, dihydroisoquinolinyl, tetrahydroisoquinolinyl, dihydrobenzofuranyl, dihydrobenzodioxynyl, tetrahydrobenzofuranyl, dihydroindolyl and the like can be mentioned.

Preferably, $X_1$ in the formula (I) can be any of the groups represented by the following formulas.

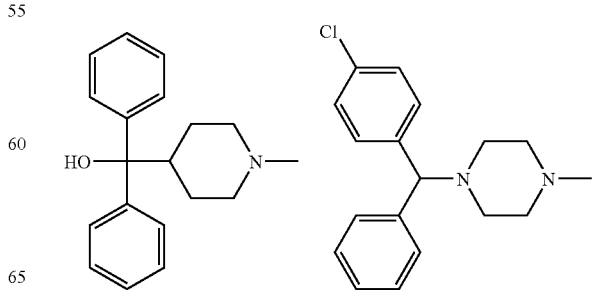

More preferably, $X_1$ in the formula (I) can be a group represented by the following formula.

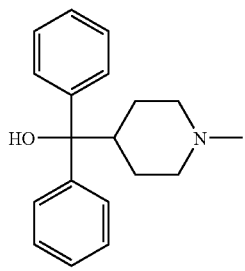

Preferably, a group represented by the following formula:

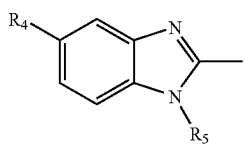

which is contained in the formula (II) can be any of the groups represented by the following formulas.

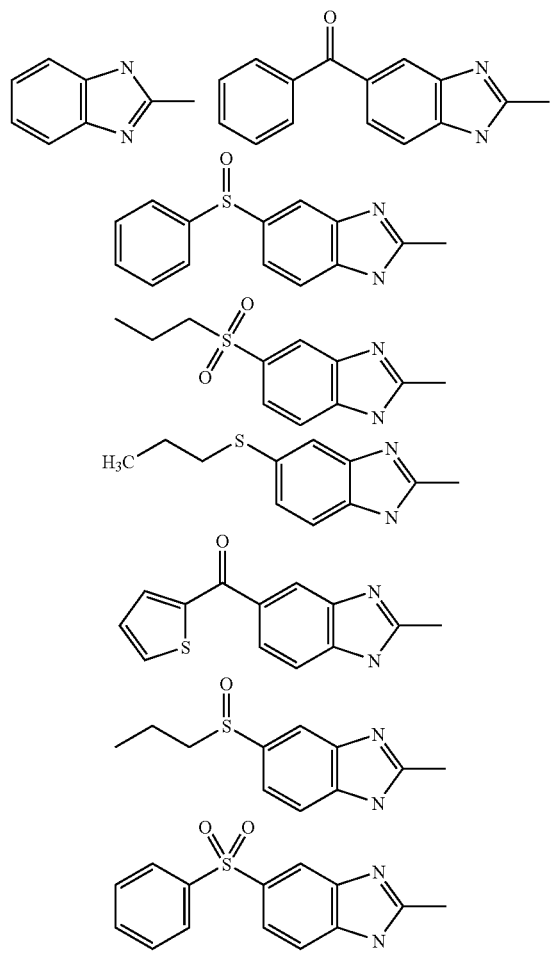

Preferable examples of $Z_{1a}$-$Z_{3a}$ include compounds represented by the following formulas:

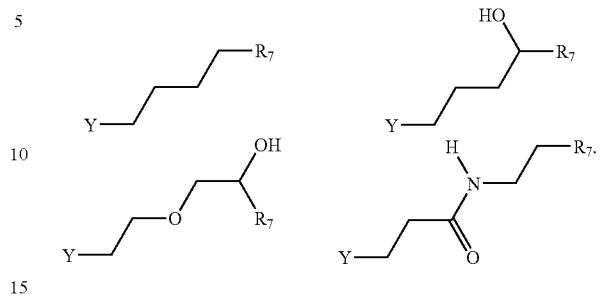

Specific examples of such $Z_{1a}$-$Z_{3a}$ include the groups represented by the following formulas:

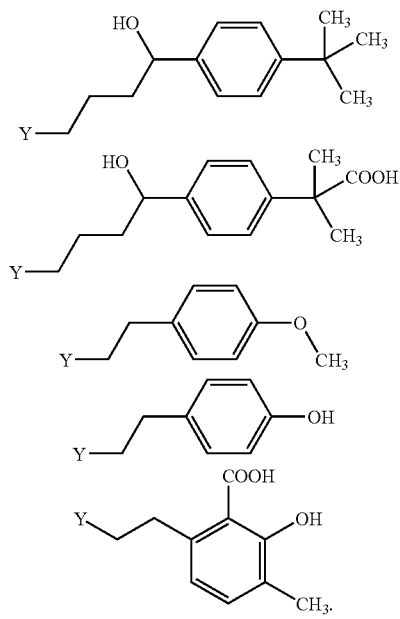

Of $Z_{1b}$-$Z_{3b}$, preferable examples of $Z_{3b}$ include the compounds represented by the following formula:
$X_3$—B—$R_8$ wherein B is alkyl having 1 to 3 carbon atoms.
Specific examples of such $Z_3$ include the groups represented by the following formula:

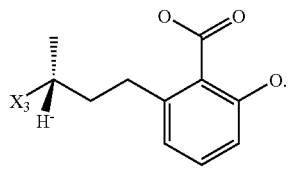

Specific examples the compound represented by $X_1$-$Z_{1a}$ include Terfenadine, α,α-diphenyl-4-piperidinomethanol and Hydroxizine.

Specific examples the compound represented by $X_2$-$Z_{2a}$ include Astemizole, Desmethyl-astemizole, 2-Amino-1-benzylbenzimidazole, Carbendazim, Oxibendazole, Albendazole, Albendazole Sulfoxide, Albendazole Sulfone, 2-Amino-5-N-propylsulphonylbenzimidazole, Mebendazole, Nocodazole, Oxfendazole, Fenbendazole Sulfone, 2-Aminobenzimidazole, Thiabendazole and Benzimidazole.

A specific example of the compound represented by $X_3$—$Z_3$ is Lasalocid sodium.

2. Screening Methods and Products Obtained by the Methods

The present invention provides screening methods for drugs, each of which comprises determining whether or not a test substance is capable of regulating the expression or function of a CARP gene. The screening methods of the present invention can be roughly divided into two types, from the viewpoint of the kind of drug screened: screening methods for substances capable of regulating an action associated with a CARP target drug (e.g., allergic conditions, liberation of chemical mediators), and screening methods for substances capable of regulating a function associated with a CARP gene. The screening methods of the present invention can also be performed in vitro, in vivo or in silico. The substance capable of regulating expression of CARP gene, which is obtained by the screening method of the present invention means the same as the substance capable of regulating the amount of CARP, and can be a substance capable of altering the amount of CARP present in a given tissue or cell, or the amount of CARP present in a given intracellular location. Accordingly, the substance capable of regulating expression of CARP gene includes, for example, a substance capable of regulating biosynthesis of CARP from a CARP gene, as well as a substance capable of regulating intracellular locality of CARP, and a substance capable of regulating CARP gene metabolism (e.g., decomposition by metabolism).

The individual screening methods are hereinafter described in detail.

2.1. Screening Methods for Substances Capable of Regulating an Action Associated with a Carp Target Drug (Screening Method I)

The present invention provides screening methods for substances capable of regulating an action associated with a CARP target drug, each of which comprises determining whether or not a test substance is capable of regulating the expression or function of a CARP gene.

The screening methods of this type are abbreviated to as "screening method I" as required.

Screening method I can be roughly divided into two types: a screening method for a substance capable of regulating an action associated with a CARP target drug, which comprises determining whether or not a test substance is capable of regulating the expression or function of a CARP gene, and selecting a test substance capable of regulating the expression or function of a CARP gene (screening method Ia), and a screening method for a substance capable of regulating an action associated with a CARP target drug (particularly an action associated with a known target molecule), which comprises determining whether or not a test substance is capable of regulating the expression or function of a CARP gene, and selecting a test substance that is incapable of regulating the expression or function of a CARP gene (screening method Ib). Screening method Ia can be useful for the development of regulators of diseases or conditions associated with a CARP target drug and the like. Screening method Ib can be useful for the development of drugs capable of regulating an action associated with a known target molecule, and showing decreased adverse effects of a CARP target drug and the like.

2.1.1. Screening Method for Substances Capable of Regulating an Action Associated with a CARP Target Drug, which Comprises Selecting a Test Substance Capable of Regulating the Expression or Function of a Carp Gene (Screening Method Ia)

The test substance subjected to this screening method may be any known compound or new compound; examples include nucleic acids, saccharides, lipids, proteins, peptides, organic small compounds, compound libraries prepared using combinatorial chemistry technique, random peptide libraries prepared by solid phase synthesis or the phage display method, or natural components derived from microorganisms, animals, plants, marine organisms and the like, and the like. The test substance may be a labeled supply or a non-labeled supply, or a mixture of a labeled supply and a non-labeled supply mixed in a specified ratio. The labeling substance is the same as described above.

In one embodiment, screening method Ia comprises the following steps (a), (b) and (c):

(a) a step for bringing the test substance into contact with CARP or mutant protein thereof;

(b) a step for measuring the functional level of CARP or mutant protein thereof in the presence of the test substance, and comparing this functional level with the functional level of CARP in the absence of the test substance;

(c) a step for selecting a test substance that alters the functional level of CARP or mutant protein thereof on the basis of the result of the comparison in step (b) above.

The methodology comprising the above-described steps (a) to (c) is abbreviated to as "methodology I" as required.

In step (a) of methodology I, a test substance is brought into contact with CARP or mutant protein thereof (hereinafter to be abbreviated CARP as necessary). Contact of the test substance with the protein can be performed by contact of isolated CARP and the test substance in solution, or contact of cells or tissue capable of expressing CARP and the test substance.

CARP can be prepared by a method known per se. For example, CARP can be isolated and purified from the above-described expression tissue. However, to prepare CARP quickly, easily, and in large amounts, and to prepare human CARP, it is preferable to prepare a recombinant protein by gene recombination technology. The recombinant protein may be prepared using a cell system or a cell-free system.

The cells capable of expressing CARP can be any cells that express CARP; examples include cells derived from the tissue in which CARP is expressed, cells transformed with a CARP expression vector and the like. Those skilled in the art are able to easily identify or prepare these cells; useful cells include primary culture cells, cell lines derivatively prepared from the primary culture cells, commercially available cell lines, cell lines available from cell banks, and the like. As the tissue capable of expressing CARP, the above-described expression tissues can be used.

In step (b) of methodology I, the functional level of CARP in the presence of the test substance is measured. The functional level is measured by a method known per se, which can measure the aforementioned function of CARP.

The functional level may also be measured on the basis of the functional level to each isoform (e.g., splicing variant) of CARP or the ratio of functional level between isoforms, rather than on the basis of the total functional level of CARP.

Next, the functional level of CARP in the presence of the test substance is compared with the functional level of CARP in the absence of the test substance. This comparison of functional level is preferably performed on the basis of the presence or absence of a significant difference. Although the functional level of CARP in the absence of the test substance may be measured prior to, or simultaneously with, the measurement of the functional level of CARP in the presence of the test substance, it is preferable, from the viewpoint of experimental accuracy and reproducibility, that the functional level be measured simultaneously.

In step (c) of methodology I, a test substance that alters the functional level of the protein is selected. The test substance that alters the functional level of the protein is capable of promoting or suppressing a function of CARP. The test substance thus selected can be useful for the regulation of a disease or condition associated with CARP target drug.

In other embodiment, screening method Ia comprises the following steps (a), (b) and (c):
(a) a step for bringing a test substance and cells allowing a measurement of the expression of the CARP gene into contact with each other;
(b) a step for measuring the expression amount of the CARP gene in the cells in contact with the test substance, and comparing this expression amount with the expression amount of the CARP gene in control cells not in contact with the test substance;
(c) a step for selecting a test substance that regulates the expression amount of the CARP gene on the basis of the results of the comparison in step (b) above.

The methodology comprising the above-described steps (a) to (c) is abbreviated to as "methodology II" as required.

In step (a) of methodology II, a test substance is brought into contact with cells allowing a measurement of the expression of the CARP gene. Contact of the test substance with the cells allowing a measurement of the expression of the CARP gene can be performed in culture medium.

"Cells allowing a measurement of the expression of the CARP gene" refers to cells enabling a direct or indirect evaluation of the expression level of a product of the CARP gene, for example, a transcription product or translation product. The cells enabling a direct evaluation of the expression level of a product of the CARP gene can be cells capable of naturally expressing the CARP gene, whereas the cells enabling an indirect evaluation of the expression level of a product of the CARP gene can be cells enabling a reporter assay on the CARP gene transcription regulatory region.

The cells capable of naturally expressing CARP gene can be any cells that potentially express CARP gene; examples include cells showing permanent expression of CARP gene, cells that express CARP gene under inductive conditions (e.g., drug treatment) and the like. Those skilled in the art are able to easily identify these cells; useful cells include primary culture cells, cell lines induced from the primary culture cells, commercially available cell lines, cell lines available from cell banks, and the like. Examples of the cell line expressing CARP include HL60, HelaS3, K-562, MOLT-4, Raji, Sw480, A549, G-361 and the like. Since CARP is known to be expressed in tissues such as the heart, skeletal muscle, brain, lungs, kidneys, liver, spleen, large intestine, small intestine and placenta, cells or cell lines derived from these tissues may be used.

The cells enabling a reporter assay on the CARP gene transcription regulatory region are cells incorporating the CARP gene transcription regulatory region and a reporter gene functionally linked to the region. The CARP gene transcription regulatory region and reporter gene are inserted in an expression vector.

The CARP gene transcription regulatory region may be any region enabling the control of the expression of CARP gene; examples include a region from the transcription initiation point to about 2 kbp upstream thereof, and a region consisting of a base sequence wherein one or more bases are deleted, substituted or added in the base sequence of the region, and that is capable of controlling the transcription of CARP gene, and the like.

The reporter gene may be any gene that encodes a detectable protein or enzyme; examples include the GFP (green fluorescent protein) gene, GUS (β-glucuronidase) gene, LUS (luciferase) gene, CAT (chloramphenicol acetyltransferase) gene and the like.

The cells transfected with the CARP gene transcription regulatory region and a reporter gene functionally linked to the region are not subject to limitation, as long as they enable an evaluation of the CARP gene transcription regulatory function, that is, as long as they enable a quantitative analysis of the expression amount of the reporter gene. However, the cells to be transfected are preferably cells capable of naturally expressing CARP gene because they are considered to express a physiological transcription regulatory factor for CARP gene, and to be more appropriate for the evaluation of the regulation of the expression of CARP gene.

The culture medium in which a test substance and cells allowing a measurement of the expression of CARP gene are brought into contact with each other is chosen as appropriate according to the kind of cells used and the like; examples include minimal essential medium (MEM), Dulbecco's modified minimal essential medium (DMEM), RPMI1640 medium, 199 medium and the like, each containing about 5 to 20% fetal bovine serum. Culture conditions are also determined as appropriate according to the kind of cells used and the like; for example, the pH of the medium is about 6 to about 8, culture temperature is normally about 30 to about 40° C., and culture time is about 12 to about 72 hours.

In step (b) of methodology II, first, the expression amount of CARP gene in the cells in contact with the test substance is measured. This measurement of expression amount can be performed by a method known per se in view of the kind of cells used and the like.

For example, when cells capable of naturally expressing CARP gene are used as the cells allowing a measurement of the expression of CARP gene, the expression amount can be measured by a method known per se with a product of CARP gene, for example, a transcription product or translation product, as the subject. For example, the expression amount of a transcription product can be measured by preparing total RNA from the cells, and performing RT-PCR, Northern blotting and the like. The expression amount of a translation product can also be measured by preparing an extract from the cells, and performing an immunological technique. Useful immunological techniques include radioisotope immunoassay (RIA), ELISA (Methods in Enzymol. 70: 419-439 (1980)), fluorescent antibody method and the like.

When cells enabling a reporter assay on the CARP gene transcription regulatory region are used as the cells allowing a measurement of the expression of CARP gene, the expression amount can be measured on the basis of the signal intensity of the reporter.

The expression amount may also be measured on the basis of the expression amount to each isoform (e.g., splicing variant) of CARP gene or the expression ratio between isoforms, rather than on the basis of the total expression amount of CARP gene.

Moreover, the expression amount can also be measured based on the locality in a given organella. The amount of CARP locally present in a cell can be measured by a method known per se. For example, CARP fused with a gene encoding fluorescent protein such as GFP gene and the like is introduced into an appropriate cell, and cultivated in a culture medium in the presence of a test substance. Then, a fluorescent signal in a given organella is observed by a confocal microscopy, and compared with a fluorescent signal in the organella in the absence of a test substance. In addition, the amount of CARP locally present in a given organella can also be measured by immunostaining using an antibody to CARP.

Next, the expression amount of CARP gene in the cells in contact with the test substance is compared with the expression amount of CARP gene in control cells not in contact with the test substance. This comparison of expression amount is preferably performed on the basis of the presence or absence of a significant difference. Although the expression amount of CARP gene in the control cells not in contact with the test substance may be measured prior to, or simultaneously with, the measurement of the expression amount of CARP gene in the cells in contact with the test substance, it is preferable, from the viewpoint of experimental accuracy and reproducibility, that the expression amount be measured simultaneously.

In step (c) of methodology II, a test substance that regulates the expression amount of CARP gene is selected. The regulation of the expression amount of CARP gene can be the promotion or suppression of the expression amount. The test substance thus selected can be useful for the regulation of an action associated with a CARP target drug.

In another embodiment, screening method Ia comprises the following steps (a), (b) and (c):
(a) a step for bringing the test substance into contact with CARP or mutant protein thereof;
(b) a step for measuring the binding ability of the test substance to the protein;
(c) a step for selecting a test substance capable of binding to the protein on the basis of the results of step (b) above.

The methodology comprising the above-described steps (a) to (c) is abbreviated to as "methodology III" as required.

In step (a) of methodology III, a test substance is brought into contact with CARP or mutant protein thereof. Contact of the test substance with the protein can be performed by mixing the test substance and the protein in solution.

CARP can be prepared by a method known per se. For example, CARP can be isolated and purified from the above-described CARP expression tissue. However, to prepare CARP quickly, easily, and in large amounts, and to prepare human CARP, it is preferable to prepare a recombinant protein by gene recombination technology. The recombinant protein may be prepared using a cell system or a cell-free system. A mutant protein having a binding ability to a CARP target drug can also be prepared easily by those of ordinary skill in the art by a method known per se. The mutant protein is as defined above.

In step (b) of methodology III, the binding ability of the test substance to the protein is measured. A measurement of the binding ability can be performed by a method known per se. In addition to the binding ability, binding strength, the concentration dependency of the test substance in the binding to the protein, and the like can further be measured. Binding strength and concentration dependency can be measured using appropriately chosen means of measurement.

A measurement of the binding ability can be performed by, for example, the SEC/MS method (size exclusion chromatography/mass analysis) (see Moy, F. J. et al., Anal. Chem., 2001, 73, 571-581). The SEC/MS method comprises (1) a step for adding a mixed multiplexed compound standard to the purified protein, and then separating the free compound and the protein by SEC, and (2) an analytical step for identifying the bound compound contained in the protein fraction by MS. The SEC/MS method is advantageous in that the binding ability can be analyzed while both the protein and the test substance are in non-modified and non-immobilized state. In the SEC/MS method, not only the binding ability of the test substance to the protein, but also the concentration dependency of the test substance in the binding to the protein and the like can be measured simultaneously.

A measurement of the binding ability can also be performed using a means for measurement based on surface plasmon resonance, for example, Biacore. Using Biacore, the binding and dissociation of a test substance to a protein immobilized on a chip are measured, and the measured values are compared with those obtained when a solution not containing the test substance is loaded on the chip. Subsequently, a test substance capable of binding to the protein is selected on the basis of the result for the binding and dissociation rate or binding level. Biacore also enables simultaneous measurements of binding strength (e.g., $K_d$ value) and the like, in addition to the binding ability of a test substance to a protein.

Other methods for measuring the binding ability include, for example, SPR-based methods or optical methods such as the Quartz Crystal Microbalance (QCM) method, the Dual Polarisation Interferometer (DPI) method, and the Coupled Waveguide Plasmon Resonance method, immunoprecipitation, isothermal titration and differential scanning calorimetry, capillary electrophoresis, energy transfer, fluorescent analytical methods such as fluorescent correlation analysis, and structural analytical methods such as X-ray crystallography and Nuclear Magnetic Resonance (NMR).

In measuring the binding ability, a CARP-binding substance can also be used as a control.

"A CARP-binding substance" is a compound capable of interacting directly with CARP or mutant protein thereof, and can be, for example, a protein, a nucleic acid, a saccharide, a lipid, or a small organic compound. Preferably, the CARP-binding substance can be CARP target drug, for example, astemizole or terfenadine or metabolite thereof, or $\alpha,\alpha$-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or derivatives thereof capable of binding to CARP (described later), and salts thereof.

As for astemizole and terfenadine, its non-metabolized form has already been clarified to be a main factor causing a harmful event (arrhythmia), and a metabolite thereof is known to be superior in the safety. As the astemizole metabolite, for example, desmethylastemizole, 4-{2-[4-(1H-benzoimidazol-2-ylamino)-piperidin-1-yl]-ethyl}-phenol, 1-(4-fluoro-benzyl)-2-{1-[2-(4-methoxy-phenyl)-ethyl]-piperidin-4-ylamino}-1H-benzoimidazol-5-ol, 3-(4-fluoro-benzyl)-2-{1-[2-(4-methoxy-phenyl)-ethyl]-piperidin-4-ylamino}-3H-benzoimidazol-5-ol, 1-(4-fluoro-benzyl)-2-{1-[2-(4-hydroxy-phenyl)-ethyl]-piperidin-4-ylamino}-1H-benzoimidazol-5-ol, 3-(4-fluoro-benzyl)-2-{1-[2-(4-hydroxy-phenyl)-ethyl]-piperidin-4-ylamino}-3H-benzoimidazol-5-ol, 4-{2-[4-(1H-benzoimidazol-2-ylamino)-piperidin-1-yl]-ethyl}-phenol, [1-(4-fluoro-benzyl)-1H-benzoimidazol-2-yl]-piperidin-4-yl-amine can be mentioned. As the terfenadine metabolite, for example, 1-[4-(2-hydroxy-1,1-dimethyl-ethyl)-phenyl]-4-[4-(hydroxy-diphenyl-methyl)-piperidin-1-yl]-butan-1-ol, 2-(4-{1-hydroxy-4-[4-(hydroxy-diphenyl-methyl)-piperidin-1-yl]-butyl}-phenyl)-2-methyl-propionic acid and diphenyl-piperidin-4-yl-methanol can be mentioned.

Although the salts may be any salts, pharmaceutically acceptable salts are preferable; examples include salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salt with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine) or salts with acidic amino acids (e.g., aspartic acid, glutamic acid) and the like.

Furthermore, the binding ability may also be measured on the basis of the binding ability to each isoform (e.g., splicing variant) of CARP or the binding ability ratio between isoforms, rather than on the basis of the total binding ability of CARP.

The binding ability can also be measured in silico. For example, a measurement of the binding ability can be performed on the basis of SBDD (Structure-Based Drug Design: SBDD) or CADD (Computer-Aided Drug Design). Examples of such screening include virtual screening, de novo design, pharmacophore analysis, QSAR (Quantitative Structure Activity Relationship) and the like. If information on the steric structure of the protein itself or the target site of the protein is required during such screening, the information on the steric structure is used, provided that the steric structure is known by a structural analytical technique such as NMR, X-ray crystallographic analysis, or synchrotron radiation analysis. If the steric structure is unknown, information obtained by a structural estimation method such as the homology method or the threading method is used. In virtual screening, a program known per se can be used; examples of the program include Dock (Kuntz, I.D. et al., Science, 1992, 257, 1078), Gold (Jones, G. et al., J. Mol. Biol., 1995, 245, 43), FlexX (Rarey, M. et al., J. Mol. Biol., 1996, 261, 470), AutoDock (Morris, G.M. et al., J. Comput. Chem., 1998, 19, 1639), ICM (Abagyan, R.A. et al., J. Comput. Chem., 1994, 15, 488) and the like.

In step (c) of methodology III, a test substance capable of binding to CARP or mutant protein thereof is selected. The test substance capable of binding to the protein is capable of promoting or suppressing a function of CARP. Thus, the selected test substance can be useful for the regulation of a disease associated with a CARP target drug.

In still another mode of embodiment, screening method Ia comprises the following steps (a), (b) and (c):

(a) a step for bringing the test substance and a CARP-binding substance into contact with CARP or mutant protein thereof;
(b) a step for measuring the binding level of the CARP-binding substance to the protein in the presence of the test substance, and comparing the binding level with that of the CARP-binding substance to the protein in the absence of the test substance;
(c) a step for selecting a test substance that alters the binding level of the CARP-binding substance to the protein on the basis of the result of the comparison in step (b) above.

The methodology comprising the above-described steps (a) to (c) is abbreviated to as "methodology IV" as required.

In step (a) of methodology IV, both a test substance and a CARP-binding substance are brought into contact with CARP or mutant protein thereof. Contact of the test substance and the CARP-binding substance with the protein can be performed by mixing the test substance, the CARP-binding substance, and the protein in solution. The order of bringing the test substance and CARP-binding substance into contact with the protein is not subject to limitation; one of them may be brought into contact with the protein at a time lag or at the same time.

CARP and a mutant protein thereof can be prepared by a method known per se. For example, preparation of the proteins can be performed by a method described in methodology III above.

The CARP-binding substance may be a labeled supply or a non-labeled supply, or a mixture of a labeled supply and a non-labeled supply mixed in a specified ratio. The labeling substance is the same as described above.

In step (b) of methodology IV, first, the binding level of the CARP-binding substance to the protein is measured in the presence of the test substance. A measurement of the binding level can be performed by a method known per se, in view of the kind of CARP-binding substance used, the presence or absence of a label, and the like. In addition to the binding level, binding strength (e.g., $K_d$ value), the concentration dependency of the test substance in the binding to the protein, and the like can further be measured. Binding strength and concentration dependency can be measured using appropriately chosen means of measurement.

A measurement of the binding level can be performed using, for example, a labeled CARP-binding substance. The CARP-binding substance bound to the protein and the unbound CARP-binding substance may be separated before measuring the binding level. More particularly, the measurement can be performed in the same manner as in methodology III.

The binding ability can be also measured on the basis of the binding ability to each isoform (e.g., splicing valiant) of CARP or the ratio of binding ability between isoforms, rather than on the basis of the total binding amount of CARP.

Next, the binding level of the CARP-binding substance to the protein in the presence of the test substance is compared with that of the CARP-binding substance to the protein in the absence of the test substance. This comparison of the binding level is preferably performed on the basis of the presence or absence of a significant difference. Although the binding level of the CARP-binding substance to the protein in the absence of the test substance may be measured prior to, or simultaneously with, the measurement of the binding level of the CARP-binding substance to the protein in the presence of the test substance, it is preferable, from the viewpoint of experimental accuracy and reproducibility, that the binding level be measured simultaneously.

In step (c) of methodology IV, a test substance that alters the binding level of the CARP-binding substance to the protein is selected. The change in the binding level can be, for example, a reduction or increase of binding level, with preference given to a reduction of binding level. Hence, the selected test substance can be useful for the regulation of an action associated with a CARP target drug.

Screening method Ia can further comprise (d) (i) a step for confirming that the selected test substance is capable of regulating, for example, promoting or suppressing, an action associated with a CARP target drug (confirmation step), or (ii) a step for identifying the kind of action exhibited by the selected test substance (identification step). The confirmation step or identification step can be performed by, for example, administering the selected test substance to a normal animal or an animal with "a disease associated with a CARP target drug" or model animal. Alternatively, these steps can also be performed by contacting a test substance with a cell, and evaluating a change in the cell phenotype after the contact. According to this identification step, the kind of "action associated with a CARP target drug" exhibited by the selected test substance can be determined, and whether or not the selected test substance can be used as either a drug or an investigational reagent, or both, and the kind of drug or investigational reagent to which the test substance is applicable can be confirmed.

Screening method Ia can also be performed using an animal. In this case, not only the expression amount of CARP gene but also the CARP expression amount (e.g., CARP amount in a given tissue or cell of animal administered with a test substance, locality in given organelle) can also be measured. Examples of the animal include mammals such as mice, rats, hamsters, guinea pigs, rabbits, dogs, and monkeys, and birds such as chickens. When a screening method of the present invention is performed using an animal, for example, a test substance that regulates the expression amount of CARP gene can be selected.

Screening method Ia enables screening of a substance capable of regulating an action associated with a CARP target drug. Hence, screening method Ia is useful for the development of prophylactic/therapeutic agents for diseases associated with a CARP target drug (e.g., allergic diseases, diseases for which regulation of the release of a chemical mediator is desired), and investigational reagents for the diseases, and the like.

2.1.2. Screening Method for Substances Capable of Regulating an Action Associated with a CARP Target Drug, which Comprises Selecting a Test Substance Incapable of Regulating the Expression or Function of a CARP Gene (Screening Method Ib)

The present invention provides a screening method for substances capable of regulating an action associated with a CARP target drug (particularly an action associated with a known target molecule and/or a pharmacological action actually shown by a CARP target drug), which comprises determining whether or not a test substance is capable of regulating the expression or function of a CARP gene, and selecting a test substance incapable of regulating the expression or function of a CARP gene (e.g., a substance having a pharmacological action actually shown by a CARP target drug and can be used for pharmaceutical use similar to that of a CARP target drug, which is free of side effects actually shown by a CARP target drug or associated with a fewer side effects).

Screening method Ib can be performed in the same manner as methodologies I to IV except that a test substance that does not cause a change or does not have the binding ability or regulatory capacity in step (c) of the above-described methodologies I to IV is selected.

In screening method Ib, the test substance to be used can be one capable of regulating the expression or function of a known target molecule or one having an action associated with a CARP target drug (particularly, a pharmacological action actually shown by a CARP target drug). Hence, screening method Ib can be used in combination with a screening method for substances capable of regulating an action associated with a known target molecule, which comprises determining whether or not the test substance is capable of regulating the expression or function of the known target molecule. The screening method for substances capable of regulating an action associated with a known target molecule can be performed in the same manner as the above-described screening method Ia. Alternatively, screening method Ib can be used in combination with a screening method of a substance capable of regulating an action associated with a CARP target drug, which includes a step of evaluating whether or not a test substance can regulate an action associated with a CARP target drug (particularly, a pharmacological action actually shown by a CARP target drug). Such screening method can be performed in the same manner as in step (d) of the aforementioned screening method Ia and using an animal or cell.

Screening method Ib enables the development of drugs having an ability to regulate an action associated with a known target molecule and/or a pharmacological action actually shown by a CARP target drug, which shows decreased side effects shown by the CARP target drug. Hence, screening method Ib is useful for the improvement of existing drugs capable of regulating an action associated with a known target molecule and the like.

2.2. Screening Method for Substances Capable of Regulating a Function Associated with the CARP Gene (Screening Method II)

The present invention provides a screening method for a substance capable of regulating a function associated with the CARP gene, which comprises determining whether or not a test substance is capable of regulating the binding ability of a CARP target drug to CARP or mutant protein thereof.

This screening method is abbreviated to as "screening method II" as required.

In one mode of embodiment, screening method II comprises the following steps (a), (b) and (c):
(a) a step for bringing a test substance and a CARP target drug into contact with CARP or mutant protein thereof capable of binding to a CARP target drug;
(b) a step for measuring the binding level of the CARP target drug to the protein in the presence of the test substance, and comparing this binding level with the binding level of the CARP target drug to the protein in the absence of the test substance;
(c) a step for selecting a test substance that alters the binding level of the CARP target drug to the protein on the basis of the results of the comparison in step (b) above.

The methodology comprising the above-described steps (a) to (c) is the same as methodology IV except that the "CARP target drug" is used instead of the "CARP-binding substance".

Screening method II enables, for example, screening of substances capable of regulating a function associated with a CARP gene, probes for CARP, and the like. Hence, screening method II is useful for the screening of prophylactic or therapeutic agents for diseases associated with CARP gene, screening of investigational reagents for the diseases, and the like.

2.3. Products Obtained by Screening Methods

The present invention provides products obtained by the above-described screening methods, for example, screening methods I and II.

A product provided by a screening method of the present invention can be a substance obtained by a screening method of the present invention, or a pharmacological regulator comprising a substance obtained by the screening method.

A product provided by a screening method of the present invention is useful for, for example, the prevention or treatment of a disease associated with a CARP target drug, or a disease associated with a CARP gene, or as an investigational reagent for the disease, and the like.

3. Regulators

The present invention provides pharmacological regulators each comprising a substance that regulates the expression or function of a CARP gene. The regulators of the present invention can be roughly divided into two types from the viewpoint of the pharmacological action to be regulated: regulators of actions associated with a CARP target drug (e.g., allergic conditions, liberation of chemical mediators), and regulators of functions associated with CARP gene. The individual regulators are hereinafter described in detail.

3.1. Regulators of Actions Associated with CARP Target Drug (Regulator I)

The present invention provides a type of regulators of actions associated with CARP target drug, each of which comprises a substance that regulates the expression or function of CARP gene.

The regulators of this type are abbreviated to as "regulator I" as required.

The substance that regulates the expression or function of CARP gene can be, for example, a substance that suppresses the expression of CARP gene. The expression refers to a state in which a CARP gene translation product is produced and is localized at the action site thereof in a functional condition. Hence, the substance that suppresses the expression may be one that acts in any stage of gene transcription, post-transcriptional regulation, translation, post-translational modification, localization and protein folding and the like.

Specifically, the substance that suppresses the expression of CARP gene is exemplified by transcription suppressor, RNA polymerase inhibitor, RNA decomposing enzyme, protein synthesis inhibitor, nuclear translocation inhibitor, protein decomposing enzyme, protein denaturant and the like; to minimize the adverse effects on other genes and proteins expressed in the cells, it is important that the substance that suppresses the expression of CARP gene be capable of specifically acting on the target molecule.

An example of the substance that suppresses the expression of CARP gene is an antisense nucleic acid to a transcription product of CARP gene, specifically mRNA or initial transcription product. "An antisense nucleic acid" refers to a nucleic acid that consists of a base sequence capable of hybridizing to the target mRNA (initial transcription product) under physiological conditions for cells that express target mRNA (initial transcription product), and capable of inhibiting the translation of the polypeptide encoded by the target mRNA (initial transcription product) in a hybridized state. The kind of antisense nucleic acid may be DNA or RNA, or a DNA/RNA chimera. Because a natural type antisense nucleic acid easily undergoes degradation of the phosphoric acid diester bond thereof by a nuclease present in the cells, an antisense nucleic acid of the present invention can also be synthesized using a modified nucleotide of the thiophosphate type (P=O in phosphate linkage replaced with P=S), 2'-O-methyl type and the like which are stable to decomposing enzymes. Other important factors for the designing of antisense nucleic acid include increases in water-solubility and cell membrane permeability and the like; these can also be cleared by choosing appropriate dosage forms such as those using liposome or microspheres.

The length of antisense nucleic acid is not subject to limitation, as long as the antisense nucleic acid is capable of specifically hybridizing to the transcription product of CARP gene; the antisense nucleic acid may be of a sequence complementary to a sequence of about 15 bases for the shortest, or the entire sequence of the mRNA (initial transcription product) for the longest. Considering the ease of synthesis, antigenicity and other issues, for example, oligonucleotides consisting of about 15 bases or more, preferably about 15 to about 30 bases, can be mentioned.

The target sequence for the antisense nucleic acid may be any sequence that inhibits the translation of CARP gene or a functional fragment thereof by being hybridized to the antisense nucleic acid, and may be the entire sequence or a partial sequence of mRNA, or the intron moiety of the initial transcription product; when an oligonucleotide is used as the antisense nucleic acid, it is desirable that the target sequence be located between the 5' terminus of the mRNA of CARP gene and the C terminus of the coding region thereof.

Furthermore, the antisense nucleic acid may be not only capable of hybridizing to a transcription product of CARP gene to inhibit its translation, but also binding to CARP gene in the form of double-stranded DNA to form a triple-strand (triplex) and inhibit the transcription to mRNA.

Another example of the substance that suppresses the expression of CARP gene is a ribozyme capable of specifically cleaving a transcription product of CARP gene, specifically mRNA or initial transcription product in the coding region (including the intron portion in the case of initial transcription product). "A ribozyme" refers to an RNA possessing enzyme activity to cleave nucleic acids. Because it has recently been shown that an oligo-DNA having the base sequence of the enzyme activity site also possesses nucleic acid cleavage activity, this term is herein used to mean a concept including DNA, as long as sequence specific nucleic acid cleavage activity is possessed. The most versatile ribozyme is self-splicing RNA, found in infectious RNAs such as those of viroid and virosoid; this self-splicing RNA is known to occur in some types, including hammerhead type and hairpin type. When ribozyme is used in the form of an expression vector comprising a DNA that encodes the same, a hybrid ribozyme wherein a sequence modified from tRNA is further linked to promote localization to cytoplasm may be used [Nucleic Acids Res., 29(13): 2780-2788 (2001)].

A still another example of the substance that suppresses the expression of CARP gene is a decoy nucleic acid. A decoy nucleic acid refers to a nucleic acid molecule that mimics a region to which a transcription regulatory factor binds; the decoy nucleic acid, which is the substance that suppresses the expression of CARP gene, can be a nucleic acid molecule that mimics a region to which a transcription activation factor for CARP gene binds.

Examples of the decoy nucleic acid include oligonucleotides modified to make them unlikely to undergo degradation in a body, such as oligonucleotides having a thiophosphoric diester bond wherein an oxygen atom in the phosphoric diester bond moiety is replaced with a sulfur atom (S-oligo), and oligonucleotides wherein the phosphoric diester bond is replaced with an uncharged methyl phosphate group, and the like. Although the decoy nucleic acid may completely match with the region to which a transcription activation factor binds, the degree of matching may be such that the transcription activation factor for CARP gene is retained. The length of the decoy nucleic acid is not subject to limitation, as long as the transcription activation factor binds thereto. The decoy nucleic acid may comprise a repeat of the same region.

Still another example of the substance that suppresses the expression of CARP gene is a double-stranded oligo-RNA, i.e. siRNA, which is complementary to a partial sequence (including the intron portion in the case of an initial transcription product) in the coding region of a transcription product of CARP gene, specifically, the mRNA or initial transcription product. It has been known that so-called RNA interference (RNAi), which is a phenomenon that if short double stranded RNA is introduced into cells, mRNA complementary to the RNA is degraded, occurs in nematodes, insects, plants and the like; recently, it has been found that this phenomenon also occurs in animal cells [Nature, 411(6836): 494-498 (2001)], which is drawing attention as an alternative technique to ribozymes. The siRNA used may be internally synthesized as described below, and a commercially available one may be used.

An antisense oligonucleotide and ribozyme can be prepared by determining the target sequence for a transcription product of CARP gene, specifically the mRNA or initial transcription product on the basis of the cDNA sequence or genomic DNA sequence of CARP gene, and by synthesizing a sequence complementary thereto using a commercially available automated DNA/RNA synthesizer (Applied Biosystems Company, Beckman Instruments Company and the like). A decoy nucleic acid and siRNA can be prepared by synthesizing a sense strand and an antisense strand in an automated DNA/RNA synthesizer, respectively, denaturing the chains in an appropriate annealing buffer solution at about 90 to about 95° C. for about 1 minute, and then annealing the chains at about 30 to about 70° C. for about 1 to about 8 hours. A longer double-stranded polynucleotide can be prepared by synthesizing a complementary oligonucleotide chain in alternative overlaps, annealing them, and then ligating them with ligase.

Another example of the substance that suppresses the expression of CARP gene is an antibody against CARP. The antibody may be a polyclonal antibody or a monoclonal antibody, and can be prepared by a well-known immunological technique. The antibody may also be a fragment of an antibody (e.g., Fab, or a recombinant antibody (e.g., single-chain antibody). Furthermore, the nucleic acid that encodes the antibody (one functionally linked to a nucleic acid having promoter activity) is also preferable as the substance that suppresses the expression of CARP gene.

The polyclonal antibody can be acquired by, for example, subcutaneously or intraperitoneally administering CARP or a fragment thereof (as required, may be prepared as a complex crosslinked to a carrier protein such as bovine serum albumin or KLH (Keyhole Limpet Hemocyanin)) as the antigen, along with a commercially available adjuvant (e.g., Freund's complete or incomplete adjuvant) to an animal about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

The monoclonal antibody can be prepared by, for example, a cell fusion method (e.g., Takeshi Watanabe, Saibou Yugouhou No Genri To Monokuronaru Koutai No Sakusei, edited by Akira Taniuchi and Toshitada Takahashi, "Monokuronaru Koutai To Gan-Kiso To Rinsho-", pages 2-14, Science Forum Shuppan, 1985). For example, the factor is administered subcutaneously or intraperitoneally along with a commercially available adjuvant to a mouse 2 to 4 times, and about 3 days after final administration, the spleen or lymph nodes are collected, and leukocytes are collected. These leukocytes and myeloma cells (e.g., NS-1, P3X63Ag8 and the like) are cell-fused to obtain a hybridoma that produces a monoclonal antibody against the factor. This cell fusion may be performed by the PEG method [J. Immunol. Methods, 81(2): 223-228 (1985)], or by the voltage pulse method [Hybridoma, 7(6): 627-633 (1988)]. A hybridoma that produces the desired monoclonal antibody can be selected by detecting an antibody that binds specifically to the antigen from the culture supernatant using a widely known EIA or RIA method and the like. Cultivation of the hybridoma that produces the monoclonal antibody can be performed in vitro, or in vivo such as in mouse or rat ascitic fluid, preferably in mouse ascitic fluid, and the antibody can be acquired from the culture supernatant of the hybridoma and the ascitic fluid of the animal, respectively.

However, in view of therapeutic efficacy and safety in humans, the antibody of the present invention may be a chimeric antibody or a humanized or human type antibody. The chimeric antibody can be prepared with reference to, for example, "Jikken Igaku (extra issue), Vol. 6, No. 10, 1988", Japanese Patent Kokoku Publication No. HEI-3-73280 and the like. The humanized antibody can be prepared with reference to, for example, Japanese Patent Kohyo Publication No. HEI-4-506458, Japanese Patent Kokai Publication No. SHO-62-296890 and the like. The human antibody can be prepared with reference to, for example, "Nature Genetics, Vol. 15, p. 146-156, 1997", "Nature Genetics, Vol. 7, p. 13-21, 1994", Japanese Patent Kohyo Publication No. HEI-4-504365, International Patent Application Publication No. WO94/25585, "Nikkei Science, June issue, pp. 40 to 50, 1995", "Nature, Vol. 368, pp. 856-859, 1994", Japanese Patent Kohyo Publication No. HEI-6-500233 and the like.

The substance that regulates the expression or function of CARP gene can also be a substance that suppresses a function of CARP gene.

Although the substance that suppresses a function of CARP gene is not subject to limitation, as long as it is capable of interfering with an action of CARP gene, it is important that the substance be capable of specifically acting on the target molecule to minimize the adverse effect on other genes and proteins. Examples of the substance that specifically suppresses a function of CARP gene include a dominant negative mutant of CARP and a nucleic acid that encodes the mutant (one functionally linked to a nucleic acid having promoter activity).

A dominant negative mutant of CARP refers to a mutant having the activity thereof reduced as a result of mutagenesis to CARP. The dominant negative mutant can have the activity thereof indirectly inhibited by competing with natural CARP. The dominant negative mutant can be prepared by introducing a mutation to a nucleic acid that encodes CARP gene. Examples of the mutation include amino acid mutations in a functional site (e.g., CARD-like site, NR box-like site, EF hand-like site) that result in a decrease in the function responsible for the site (e.g., deletion, substitution, and addition of one or more amino acids). The mutation can be introduced by a method known per se using PCR or a commonly known kit.

Provided that the substance that suppresses the expression of CARP gene is a nucleic acid molecule, the regulator of the present invention can have an expression vector that encodes the nucleic acid molecule as the active ingredient thereof. In the expression vector, an oligonucleotide or polynucleotide that encodes the above-described nucleic acid molecule must be functionally linked to a promoter capable of exhibiting promoter activity in the cells of the recipient mammal. Any promoter capable of functioning in the recipient mammal to be the administration subject can be used; examples include viral promoters such as the SV40-derived early promoter, cytomegalovirus LTR, Rous sarcoma virus LTR, MoMuLV-derived LTR, and adenovirus-derived early promoter, and mammalian structural protein gene promoters such as the β-actin gene promoter, PGK gene promoter, and transferrin gene promoter, and the like.

The expression vector preferably comprises a transcription termination signal, that is, a terminator region, downstream of the oligo (poly)nucleotide that encodes the nucleic acid molecule. The expression vector may further comprise a selection marker gene for selecting transformant cells (genes that confer resistance to drugs such as tetracycline, ampicillin, kanamycin, hygromycin, and phosphinothricin, gene that compensate for auxotrophic mutation, and the like).

Although the basic backbone vector used as the expression vector is not subject to limitation, vectors suitable for administration to mammals such as humans include viral vectors such as retrovirus, adenovirus, adeno-associated virus, herpesvirus, vaccinia virus, poxvirus, poliovirus, Sindbis virus, and Sendai virus. Adenovirus has advantageous features, including the very high gene transduction efficiency and possibility of introduction to non-dividing cells. Because incorporation of the introduced gene to host chromosome is very rare, however, gene expression is transient, usually lasting for about 4 weeks. In view of the sustainability of therapeutic effect, it is also preferable to use adeno-associated virus, which offers relatively high gene transduction efficiency, which can be introduced to non-dividing cells, and which can be incorporated in chromosomes via a inverted terminal repeat sequence (ITR).

The substance that regulates the expression or function of CARP can also be CARP target drug, for example, astemizole or terfenadine or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP (described later), or a salt thereof.

Regulator I, in addition to a substance that regulates the expression or function of CARP gene, can comprise any carrier, for example, a pharmaceutically acceptable carrier.

Examples of the pharmaceutically acceptable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, is sucrose, and starch; disintegrants such as starch, carboxymethylcellulose, hydroxypropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin ammonium salt, glycine, and orange powder; preservatives such as sodium benzoate, sodium hydrogen sulfite, methyl paraben, and propyl paraben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao fat, polyethylene glycol, and kerosene, and the like.

Preparations suitable for oral administration include liquids comprising an effective amount of substance dissolved in a diluent such as water, physiological saline, or orange juice, capsules, sachets or tablets comprising an effective amount of substance in the form of solid or granules, suspensions comprising an effective amount of substance suspended in an appropriate dispersant, emulsions comprising a solution in which an effective amount of substance dissolved, dispersed and emulsified in an appropriate dispersant, and the like.

Preparations suitable for parenteral administration (e.g., subcutaneous injection, intramuscular injection, topical injection, intraperitoneal injection, and the like) include aqueous and non-aqueous isotonic sterile injection liquids, which may comprise an antioxidant, a buffer solution, a bacteriostatic agent, an isotonizing agent and the like. Other examples are aqueous and non-aqueous sterile suspensions, which may comprise a suspending agent, a solubilizer, a thickening agent, a stabilizer, an antiseptic and the like. The preparation can be included in a container in a unit dose or multiple doses like an ampoule or vial. It is also possible to lyophilize the active ingredient and a pharmaceutically acceptable carrier and preserve them in a state that only requires dissolving or suspending in a suitable sterile vehicle immediately before use.

The dose of regulator I varies depending on the activity and kind of the active ingredient, severity of the disease, the animal species to be the administration subject, drug acceptability, body weight and age of the administration subject, and the like, it is generally about 0.001 to about 500 mg/kg a day for an adult based on the amount of the active ingredient.

Regulator I enables the regulation, for example, suppression or promotion, of an action associated with a CARP target drug. Hence, regulator I is useful for the prevention/treatment of diseases associated with a CARP target drug (e.g., allergic diseases, diseases for which regulation of the release of a chemical mediator is desired), and as an investigational reagent for the diseases.

3.2. Regulator of Function Associated with the CARP Gene (Regulator II)

The present invention provides a regulator of a function associated with the CARP gene, which comprises a CARP target drug.

This regulator is abbreviated to as "regulator II" as required.

The CARP target drug can be described above, for example, can be astemizole or terfenadine or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, ia thiabendazole, benzimidazole or lasalocid, or a derivative thereof capable of binding to CARP (described below), or a salt thereof.

Regulator II can comprise, in addition to CARP target drug, any carrier, for example, a pharmaceutically acceptable carrier. The dose of regulator II is the same as that of regulator I.

Regulator II enables the regulation, for example, suppression or promotion, of a function associated with a CARP gene. Hence, regulator II is useful for the prophylaxis and treatment of a disease associated with CARP gene, and as an investigational reagent for the disease, and the like.

4. Derivative Production Method and Product Obtained by the Method

The present invention provides production methods for drug derivatives, each of which comprises derivatizing a drug so that the expression or function of the CARP gene can be regulated, and products obtained using the production methods. The production methods of the present invention can be roughly divided from the viewpoint of the kind of action or function of the derivative obtained into two types: production methods for a drug derivative capable of regulating an action associated with a CARP target drug (e.g., allergic symptoms, release of chemical mediators), and production methods for a drug derivative capable of regulating a function associated with the CARP gene. The individual production methods are hereinafter described in detail.

4.1. Production Method for Drug Derivative Capable of Regulating An Action Associated with a CARP Target Drug (Production Method I)

The present invention provides a production method for a drug derivative capable of regulating an action associated with a CARP target drug, which comprises derivatizing a drug so that the expression or function of the CARP gene can be regulated.

This production method is abbreviated to as "production method I" as required.

Derivatization means that a compound obtained by replacing a particular atom or group in a lead compound with another atom or group, or a compound obtained by subjecting a lead compound to an addition reaction, is virtually or actually synthesized. For example, the lead compound can be a CARP target drug. The CARP target drug can be described above, for example, can be astemizole or terfenadine or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP (described below), or a salt thereof.

The derivatization of CARP target drug can be performed so that the regulatory capability for the expression or function of CARP gene is retained, and as required, in view of other properties of the derivative obtained, such as water solubility/lipid solubility, stability, disposition, bioavailability, toxicity and the like. The derivatization of CARP target drug can be performed so that, for example, the regulatory capability for the expression or function of CARP gene can be increased. The derivatization of CARP target drug can also be performed so that a function associated with a CARP gene can be regulated.

The derivatization of CARP target drug such that the regulatory capability for the expression or function of CARP gene is retained can be performed on the basis of, for example, SBDD (Structure-Based Drug Design) and CADD (Computer-Aided Drug Design). Examples of the design include virtual screening, de novo design, pharmacophore analysis, QSAR (Quantitative Structure Activity Relationship) and the like. If information on the steric structure of the protein itself or the target site of the protein is required during such designing, information on the steric structure is used provided that the steric structure is known by a structural analytical technique such as NMR, X-ray crystallographic analysis, or synchrotron radiation analysis. If the steric structure is unknown, information obtained by a structural predictive method such as the homology method or the threading method is used. In virtual screening, a program known per se is used; examples of the program include DOCK (Kuntz, I.D. et al., Science, 1992, 257, 1078), Gold (Jones, G. et al., J. Mol. Biol., 1995, 245, 43), FlexX (Rarey, M. et al., J. Mol. Biol., 1996, 261, 470), AtutoDock (Morris, G.M. et al., J. Comput. Chem., 1998, 19, 1639), ICM (Abagyan, R.A. et al., J. Comput. Chem., 1994, 15, 488) and the like.

The derivatization of CARP target drug such that the regulatory capability for the expression or function of CARP gene is retained can also be performed on the basis of, for example, biological verification. In this case, for example, the above-described methodologies I to IV can be used. Furthermore, one of the above-described methods such as SBDD and CADD, and biological verification may be used in combination.

The particular atom in CARP target drug, which is substituted for producing the derivative, may be any atom present in the lead compound, exemplified by a hydrogen atom, a halogen atom (e.g., fluorine atom, chlorine atom, bromine atom, iodine atom), an oxygen atom, a sulfur atom, a nitrogen atom, a carbon atom and the like.

The particular group in CARP target drug, which is substituted for producing the derivative, may be any group present in CARP target drug, and can, for example, be a group having a molecular weight of 1 to 500, preferably 1 to 300, more preferably 1 to 200, most preferably 1 to 100. Examples of the particular group include an optionally substituted $C_1$ to $C_8$ hydrocarbon group, an optionally substituted $C_1$ to $C_8$ acyl group, an optionally substituted aromatic or non-aromatic $C_3$ to $C_{14}$ hydrocarbon cyclic group, or an optionally substituted aromatic or non-aromatic $C_3$ to $C_{14}$ heterocyclic group, an amino group, an amino group mono- or di-substituted by an alkyl group having 1 to 4 carbon atoms or an acyl group having 2 to 8 carbon atoms, an amidino group, a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, an alkoxycarbonyl group having 2 to 8 carbon atoms, a hydroxy group, an alkoxy group having 1 to 6 carbon atoms optionally substituted by 1 to 3 halogen atoms, an alkenyloxy group having 2 to 5 carbon atoms optionally substituted by 1 to 3 halogen atoms, a cycloalkyloxy group having 3 to 7 carbon atoms, an aralkyloxy group having 7 to 9 carbon atoms, an aryloxy group having 6 to 14 carbon atoms, a thiol group, an alkylthio group having 1 to 6 carbon atoms optionally substituted by 1 to 3 halogen atoms, an aralkylthio group having 7 to 9 carbon atoms, an arylthio group having 6 to 14 carbon atoms, a sulfo group, a cyano group, an azido group, a nitro group, a nitroso group and the like.

The optionally substituted $C_1$ to $C_8$ hydrocarbon group can, for example, be an optionally substituted $C_1$ to $C_8$ alkyl group, an optionally substituted $C_2$ to $C_8$ alkenyl group, or an optionally substituted $C_2$ to $C_8$ alkynyl group.

The $C_1$ to $C_8$ alkyl group in the optionally substituted $C_1$ to $C_8$ alkyl group may be linear or branched, preferably having 1 to 6 carbon atoms; examples include methyl, ethyl, propyl, isopropyl, butyl, isobutyl, sec-butyl, tert-butyl and the like.

The $C_2$ to $C_8$ alkenyl group in the optionally substituted $C_2$ to $C_8$ alkenyl group may be linear or branched, preferably having 2 to 6 carbon atoms; examples include ethenyl, 1-propenyl, 2-propenyl, 2-methyl-1-propenyl, 1-butenyl, 2-butenyl, 3-butenyl and the like.

The $C_2$ to $C_8$ alkynyl group in the optionally substituted $C_2$ to $C_8$ alkynyl group may be linear or branched, preferably having 2 to 6 carbon atoms; examples include ethynyl, 1-propynyl, 2-propynyl, 1-buthynyl, 2-buthynyl, 3-buthynyl and the like.

The $C_1$ to $C_8$ acyl group in the optionally substituted $C_1$ to $C_8$ acyl group may be linear or branched, preferably having 2 to 6 carbon atoms; examples include formyl, acetyl, propinoyl, butanoyl, 2-methylpropinoyl and the like.

The aromatic $C_3$ to $C_{14}$ hydrocarbon cyclic group in the optionally substituted aromatic $C_3$ to $C_{14}$ hydrocarbon cyclic group may be monocyclic, bicyclic or tricyclic, preferably having 3 to 12 carbon atoms; examples include phenyl and naphthyl.

The non-aromatic $C_3$ to $C_{14}$ hydrocarbon cyclic group in the optionally substituted non-aromatic $C_3$ to $C_{14}$ hydrocarbon cyclic group may be saturated or unsaturated monocyclic, bicyclic or tricyclic, preferably having 3 to 12 carbon atoms; examples include cycloalkyl groups (e.g., cyclopropyl, cyclobutyl, cyclopentyl, cyclohexyl, cycloheptyl, cyclooctyl), cycloalkenyl groups (e.g., 2-cyclopenten-1-yl, 3-cyclopenten-1-yl, 2-cyclohexen-1-yl, 3-cyclohexen-1-yl), cycloalkadienyl groups (e.g., 2,4-cyclopentadien-1-yl, 2,4-cyclohexadien-1-yl, 2,5-cyclohexadien-1-yl) and the like.

The aromatic $C_3$ to $C_{14}$ heterocyclic group in the optionally substituted aromatic $C_3$ to $C_{14}$ heterocyclic group is a monocyclic, bicyclic or tricyclic aromatic heterocyclic group containing 1 to 5 hetero atoms selected from among oxygen atoms, sulfur atoms and nitrogen atoms, in addition to carbon atoms, as the ring-forming atoms, preferably having 3 to 12 carbon atoms. Examples of the monocyclic aromatic $C_3$ to $C_{14}$ heterocyclic group include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl and the like. Examples of the bicyclic or tricyclic aromatic heterocyclic group include benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthaladinyl, naphthylizinyl, purinyl, pteridinyl, carbazolyl, α-carbonylyl, β-carbonylyl, γ-carbonylyl, acrydinyl, phenoxazinyl, phenothiazinyl, phenadinyl, phenoxathiinyl, thianthrenyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

The non-aromatic $C_3$ to $C_{14}$ heterocyclic group in the optionally substituted non-aromatic $C_3$ to $C_{14}$ heterocyclic group is a monocyclic, bicyclic or tricyclic saturated or unsaturated heterocyclic group containing 1 to 5 hetero atoms selected from among oxygen atoms, sulfur atoms and nitrogen atoms, in addition to carbon atoms, as the ring-forming atoms, preferably having 3 to 12 carbon atoms; examples include oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like.

The kind of the substituent in any group optionally substituted can be the same as the particular group in CARP target drug (described above), which is substituted for producing the derivative.

The number of particular atoms or groups in CARP target drug, which is substituted for producing the derivative is any one, as long as the derivative produced is capable of regulating the expression or function of the CARP gene, for example, as long as it is capable of binding to CARP, and can be, for example, 1 to 10, preferably 1 to 5, more preferably 1 to 3, further more preferably 1 to 2, most preferably 1.

The kind of a particular atom or group used for substitution (i.e., an atom or group introduced to the substitution site) can be the same as the particular atom or group in a CARP target drug, which is substituted for producing the derivative.

The atom or group added to CARP target drug for producing the derivative (i.e., an atom or group used in the addition reaction) is one permitting an addition reaction, for example, an atom such as the hydrogen atom or the halogen atom, or a group capable of acting as a nucleophile or electrophile, out of the particular atoms or groups in CARP target drug (described above), which is substituted for producing the derivative.

The number of atoms or groups added to CARP target drug for producing the derivative is any one, as long as the derivative produced is capable of regulating the expression or function of the CARP gene, for example, as long as it is capable of binding to CARP, and can be, for example, less than 6, preferably less than 4, more preferably less than 2.

Production method I is useful for, for example, the development of prophylactic/therapeutic agents for diseases associated with a CARP target drug (e.g., allergic diseases, diseases for which regulation of the release of a chemical mediator is desired), or investigational reagents for the diseases, and the like.

4.2. Production Method for Drug Derivative Capable of Regulating a Function Associated with the CARP Gene (Production Method II)

The present invention provides a production method for a drug derivative capable of regulating a function associated with the CARP gene, which comprises derivatizing a drug so that the binding ability thereof to CARP or mutant protein thereof can be regulated.

This production method is abbreviated to as "production method II" as required.

The derivatization of the drug can be performed so that the binding ability thereof to CARP or mutant protein thereof is retained, and as required, in view of other properties of the derivative obtained, such as water solubility/lipid solubility, stability, disposition, bioavailability, toxicity and the like. The derivatization of the drug can be performed so that, for example, the binding ability thereof can be increased.

The derivatization of the drug such that the binding ability thereof is retained can be performed on the basis of, for example, SBDD and CADD.

The derivatization of the drug such that the binding ability thereof is retained can also be performed on the basis of, for example, biological verification. In this case, for example, derivatization can be performed in the same manner as the above-described methodology IV. Furthermore, the above-described methods such as SBDD and CADD, and biological verification may be used in combination.

The choice of a particular atom and group in the lead compound substituted for producing a derivative, and their numbers, can be the same as those described above. The particular atom or group used for the substitution (i.e., atom or group introduced to the substitution site), the atom or group added to the drug for producing a derivative (i.e., atom or group used for the addition reaction), and their numbers are also the same as those described above.

Production method II is useful for the development of prophylactic/therapeutic agents for diseases associated with the CARP gene, or investigational reagents for the diseases, and the like.

4.3. Products Obtained by the Production Methods of the derivative

The present invention provides products obtained by the above-described production methods I and II.

The products provided by the above-described production methods can be derivatives of CARP target drugs obtained by the production methods of the present invention, and regulators of pharmacological actions (described above), which comprises the derivatives.

The products provided by the above-described production methods are useful for, for example, the prevention/treatment of diseases associated with a CARP target drug, or diseases associated with the CARP gene, or as investigational reagents for the diseases, and the like.

5. Complex and Production Method Therefor

The present invention provides a complex comprising a drug and CARP or mutant thereof.

The drug can be an above-described CARP target drug, for example, can be astemizole or terfenadine or metabolite thereof, or α,α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP (described below), or a salt thereof.

The present invention also provides a method of producing a complex comprising a drug and CARP or mutant thereof, which comprises bringing the drug and CARP or mutant thereof into contact with each other. This contact can be performed by, for example, mixing the drug and the protein in solution.

The complex of the present invention and the method of producing the complex can be useful in, for example, performing the screening methods of the present invention or the derivative production method of the present invention, or in cases where the complex is structurally analyzed to extensively investigate the mode of interaction between a drug and a protein, and the like.

6. Kit

The present invention provides a kit comprising a drug or a salt thereof.

In one embodiment, the kit of the present invention comprises the following (i) and (ii):

(i) a drug or a salt thereof;
(ii) CARP or mutant protein thereof, a nucleic acid that encodes the protein, an expression vector comprising the nucleic acid, cells enabling a measurement of the expression of a CARP gene, or an expression vector comprising the transcription regulatory region of a CARP gene and a reporter gene functionally linked to the region.

Provided that the kit of the present invention comprises a protein, the protein is not in the form of a complex with a drug.

The expression vector, the cells enabling a measurement of the expression of a CARP gene, the transcription regulatory region of the CARP gene, and the reporter gene functionally linked to the region, are the same as those described above (see, e.g., "2. Screening method, and product obtained by the method").

The above-described kit of the present invention can be useful in, for example, performing the screening methods of the present invention, the derivative production method of the present invention, and the complex production method of the present invention and the like.

7. Determination Methods and Determination Kits for the Onset or Risk of Onset of Disease The present invention provides determination methods and determination kits for the onset or risk of onset of a specified disease. The determination methods and determination kits of the present invention can be roughly divided from the viewpoint of the subject to be measured into two types: those based on measurements of expression amounts and those based on measurements of polymorphism. The determination methods and determination kits of the present invention can also be roughly divided from the viewpoint of the disease for which a determination of the onset or risk of onset is desired into two types: those for the onset or risk of onset of a disease associated with a CARP target drug (e.g., allergic diseases, diseases for which regulation of the release of a chemical mediator is desired), and those for the onset or risk of onset of a disease associated with the CARP gene. The individual determination methods and test kits are hereinafter described in detail.

7.1. Determination Methods and Determination Kits for the Onset Or Risk of Onset of Disease on the Basis of Measurement of the Expression Amount of CARP Gene 7.1.1. Determination Method for the Onset or Risk of Onset of Disease Associated with CARP Target Drug on the Basis of Measurement of the Expression Amount of Carp Gene (Determination Method I)

The present invention provides a determination method for the onset or risk of onset of a disease associated with CARP target drug, which comprises measuring the expression amount of CARP gene.

This determination method is abbreviated to as "determination method I" as required.

In one embodiment, determination method I comprises the following steps (a) and (b):
(a) a step for measuring the expression amount of CARP gene in a biological sample collected from an animal;
(b) a step for evaluating the onset or likelihood of onset of a disease associated with CARP target drug on the basis of the expression amount of CARP gene.

The methodology comprising the above-described steps (a) and (b) is abbreviated to as "methodology V" as required.

In step (a) of methodology V, the expression amount of CARP gene in a biological sample collected from an animal is measured. Although the animal is not particularly limited, mammals such as laboratory animals such as mice, rats, hamsters, guinea pigs, and rabbits, domestic animals such as swine, bovine, goat, horses, and sheep, companion animals such as dogs and cats, and primates such as monkeys, orangutans, chimpanzees, and humans can be mentioned.

The biological sample may be any sample containing a tissue expressing CARP gene. The tissue expressing CARP gene is the same as described above.

The expression amount of CARP gene can be measured by a method known per se with a product, for example, a transcription product or translation product, of CARP gene, as the subject.

In step (b) of methodology V, a evaluation is made whether or not the animal is suffering from a disease associated with CARP target drug on the basis of the expression amount of CARP gene. Specifically, first, the measured expression amount of CARP gene is compared with the expression amount of CARP gene in an animal that has not affected the disease associated with CARP target drug (e.g., a normal animal). This comparison of expression amount is preferably performed on the basis of the presence or absence of a significant difference. The expression amount of CARP gene in an animal that has not affected the disease associated with CARP target drug can be determined by a method known per se.

Next, on the basis of the result of the comparison of the expression amount of CARP gene, a judgment is made whether or not the animal is possibly suffering from a disease associated with CARP target drug, or is likely or unlikely to suffer from the same in the future. It is known that in animals that have contracted a particular disease, a change in the expression of the gene associated with the disease is often observed. It is also known that prior to the onset of a particular disease, a change in the expression of the particular gene is often observed. Hence, by analyzing the expression amount of CARP gene, it is possible to determine the onset or likelihood of onset of the disease associated with CARP target drug.

Determination method I enables a determination of the presence or absence of a disease associated with CARP target drug (e.g., allergic diseases, a disease for which regulate of release of a chemical mediator is desired), or the likelihood of affecting the disease. Hence, determination method I is useful for, for example, the easy and early detection of the disease to and the like.

7.1.2. Determination Kit for the Onset or Risk of Onset of Disease Associated with CARP Target Drug on the Basis of Measurement of Expression Amount of CARP Gene (Determination Kit I)

The present invention provides a determination kit that enables the easy conduct of determination method I.

This determination kit is abbreviated to as "determination kit I" as required.

In one embodiment, determination kit I comprises the following (i) and (ii):
(i) a means enabling a measurement of the expression amount of CARP gene;
(ii) a medium recording the relationship between a disease associated with CARP target drug and the expression amount of CARP gene.

The means enabling a measurement of the expression amount of CARP gene is not subject to limitation, as long as it allows a quantitation of the expression amount of CARP gene; for example, such means are roughly divided into means capable of quantifying CARP (e.g., antibody, CARP target drug), and means capable of quantifying a transcription product of CARP gene (e.g., nucleic acid probe, primer pair). The means may be labeled with a labeling substance. Provided that the means is not labeled with a labeling substance, the determination kit of the present invention may further comprise the labeling substance. The labeling substance is the same as described above.

Determination kit I enables a determination of the presence or absence of a disease associated with CARP target drug (e.g., allergic diseases, a disease for which regulate of release of a chemical mediator is desired), or the likelihood of affecting the disease. Hence, determination kit I is useful for, for example, the easy and early detection of the disease and the like.

7.2. Determination Methods and Determination Kits for the Risk of Onset of Disease on the Basis of Measurement of Polymorphism of CARP Gene 7.2.1. Determination Method for the Risk of Onset of Disease Associated with CARP Target Drug on the Basis of Measurement of Polymorphism of CARP Gene (Determination Method II)

The present invention provides a determination method for the risk of onset of a disease associated with CARP target drug, which comprises measuring the polymorphism of CARP gene.

This determination method is abbreviated to as "determination method II" as required.

In one embodiment, determination method II comprises the following steps (a) and (b):
(a) a step for measuring the polymorphism of CARP gene in a biological sample collected from an animal;
(b) a step for evaluating the likelihood of the onset of a disease associated with CARP target drug on the basis of the type of polymorphism.

The methodology comprising the above-described steps (a) and (b) is abbreviated to as "methodology VI" as required.

In step (a) of methodology VI, the type of polymorphism of CARP gene in a biological sample collected from an animal is measured. The animal is the same as described above.

Although the biological sample used may be one described with respect to methodology V above, this methodology VI enables the use of any tissue containing genomic DNA such as hair, nails, skin or mucosa as the biological sample. In view of the ease of procurement, burden on the human body and the like, the biological sample is preferably a sample of hair, nails, skin, mucosa, blood, plasma, serum, saliva and the like.

A polymorphism of CARP gene means a mutation found at a frequency in the nucleotide sequence of the genomic DNA comprising CARP gene in a certain population, and can be one or more DNA substitutions, deletions, or additions (e.g., SNP, haplotype) in the genomic DNA comprising CARP gene, and a repeat, inversion, translocation and the like of the genomic DNA. Various types of polymorphism of CARP gene are registered with known databases, for example, H-Inv DB and the like. The type of polymorphism of CARP gene used in this determination method is a mutation in a nucleotide sequence whose frequency differs between animals suffering from a disease associated with CARP target drug and non-suffering animals out of all types of polymorphism in CARP gene, and can be, for example, one that alters the expression of CARP gene or alters a function associated with a CARP gene (e.g., the binding ability of CARP to CARP target drug). Such types of polymorphism can be determined by a method known per se such as linkage analysis.

A determination of the type of polymorphism can be performed by a method known per se. For example, the RFLP (restriction fragment length polymorphism) method, the PCR-SSCP (single-stranded DNA conformation polymorphism) analysis method, the ASO (allele specific oligonucleotide) hybridization method, the TagMan PCR method, the invader method and the like can be used.

In step (b) of methodology VI, an evaluation of the level of likelihood of affecting a disease associated with CARP target drug in an animal is made on the basis of the type of polymorphism. It is known that animals susceptible to a particular disease often have a particular type of polymorphism in the gene associated with the disease. Hence, it is possible to determine the likelihood of the onset of a disease associated with CARP target drug by polymorphism analysis.

Determination method II enables a determination of the likelihood of affecting a disease associated with CARP target drug (e.g., allergic diseases, a disease for which regulate of release of a chemical mediator is desired). Hence, determination method II is useful for the provision of an incentive for improving one's lifestyle for the purpose of preventing the disease and the like.

7.2.2. Determination Kit for the Risk of Onset of Disease Associated with CARP Target Drug on the Basis of Measurement of Polymorphism of CARP Gene (Determination Kit II)

The present invention also provides a determination kit that enables the easy conduct of determination method II.

This determination kit is abbreviated to as "determination kit II" as required.

In one embodiment, determination kit II comprises the following (i) and (ii):
(i) a means enabling a measurement of the polymorphism of CARP gene (e.g., nucleic acid probe, primer pair);
(ii) a medium recording the relationship between a disease associated with CARP target drug and the polymorphism of the CARP gene.

Determination kit II enables a determination of the likelihood of affecting a disease associated with CARP target drug (e.g., allergic diseases, a disease for which regulate of release of a chemical mediator is desired). Hence, determination kit II is useful for the provision of an incentive for improving one's lifestyle for the purpose of preventing the disease and the like.

7.2.3. Method of Determining the Risk of Onset of Disease Associated with CARP Gene on the Basis of Measurement of Polymorphism of CARP Gene (Determination Method III)

The present invention provides a determination method for the risk of onset of a disease associated with CARP gene, which comprises measuring the polymorphism of CARP gene.

This determination method is abbreviated to as "determination method III" as required.

In one embodiment, determination method III Comprises the following steps (a) and (b):
(a) a step for measuring the type of the polymorphism of CARP gene in a biological sample collected from an animal;
(b) a step for evaluating the likelihood of the onset of a disease associated with CARP gene on the basis of the type of polymorphism.

In determination method III, the type of polymorphism used to determine the risk of onset alters the binding ability of CARP to CARP target drug. The type of polymorphism can be determined by a method known per se such as binding assay.

The methodology comprising steps (a) and (b) above in determination method III is the same as methodology VI except for the type of polymorphism of CARP gene to be measured.

Determination method III enables a determination of the likelihood of affecting a disease associated with CARP gene. Hence, determination method III is useful for the provision of an incentive for improving one's lifestyle for the purpose of preventing the disease and the like.

7.2.4. Determination Kit for the Risk of Onset of Disease Associated with CARP Gene on the Basis of Measurement of Polymorphism of CARP Gene (Determination Kit III)

The present invention also provides a determination kit that enables the easy conduct of determination method III.

This determination kit is abbreviated to as "determination kit III" as required.

In one embodiment, determination kit III comprises the following (i) and (ii):

(i) a means enabling a measurement of the polymorphism of CARP gene;
(ii) a medium recording the relationship between a disease associated with CARP gene and the polymorphism of CARP gene.

In determination kit III, the type of polymorphism used to determine the risk of onset is one that alters the binding ability of CARP to CARP target drug. The type of polymorphism can be determined by a method known per se such as binding assay.

The constituents of determination kit III are the same as those of determination kit II except for the type of polymorphism of CARP gene to be measured.

Determination kit III enables a determination of the likelihood of affecting a disease associated with CARP gene. Hence, determination kit III is useful for the provision of an incentive for improving one's lifestyle for the purpose of preventing the disease and the like.

8. Determination Methods and Determination Kits for Susceptibility to Drugs

The present invention provides determination methods and determination kits for susceptibility to a drug. The determination methods and determination kits of the present invention can be roughly divided into determination methods and determination kits based on measurement of expression amount, and determination methods and determination kits based on measurement of polymorphism. Furthermore, they are classified into determination methods and determination kits for a disease associated with CARP target drug (e.g., allergic diseases, a disease for which regulate of release of a chemical mediator is desired), and determination methods and determination kits for a disease associated with CARP gene, from the viewpoint of a disease for which a determination of susceptibility is desired. The individual determination methods and determination kits are hereinafter described in detail.

8.1. Determination Methods and Determination Kits for Susceptibility to Drugs on the Basis of Measurement of the Expression Amount of CARP Gene 8.1.1. Determination Method for Susceptibility to Carp Target Drug in Disease Associated with Carp Target Drug on the Basis of Measurement of the Expression Amount of Carp Gene (Determination Method IV)

The present invention provides a determination method for susceptibility to CARP target drug in a disease associated with CARP target drug, which comprises measuring the expression amount of CARP gene.

This determination method is abbreviated to as "determination method IV" as required.

In one embodiment, determination method IV comprises the following steps (a) and (b):

(a) a step for measuring the expression amount of CARP gene in a biological sample collected from an animal;
(b) a step for predicting the effect of CARP target drug on the basis of the expression amount of CARP gene.

The methodology comprising the above-described steps (a) and (b) is abbreviated to as "methodology VII" as required.

Step (a) of methodology VII is the same as step (a) of methodology V.

In step (b) of methodology VII, the possible effect of CARP target drug on animals is evaluated on the basis of the expression amount of CARP gene. Specifically, first, the measured expression amount of CARP gene is checked against data on the correlation between the expression amount of CARP gene and susceptibility to CARP target drug. The correlation between the expression amount of CARP gene and susceptibility to CARP target drug can be determined by a method known per se.

Next, from the result of the checking, susceptibility to CARP target drug is estimated. It is considered that in animals expressing a CARP gene at high levels, their susceptibility to the drug is high (or low), and that in animals expressing the same at low levels, their susceptibility is low (or high). Hence, it is possible to determine the susceptibility to CARP target drug by analyzing the expression amount of CARP gene. For example, provided that CARP target drug is a drug, the likelihood or unlikelihood of obtainment of desired effect of the drug, or the probability of onset of adverse effect of a drug, can be determined.

Determination method IV enables a determination of susceptibility to CARP target drug. Hence, determination method IV is useful for, for example, the evaluation of an action of CARP target drug on a particular animal, and the like.

8.1.2. Determination Kit for Susceptibility to CARP Target Drug in Disease Associated with CARP Target Drug on the Basis of Measurement of the Expression Amount of CARP Gene (Determination Kit IV)

The present invention provides a determination kit that enables the easy conduct of determination method IV.

This determination kit is abbreviated to as "determination kit IV" as required.

In one embodiment, determination kit IV comprises the following (i) and (ii):

(i) a means enabling a measurement of the expression amount of CARP gene;
(ii) a medium recording the relationship between the effect of CARP target drug and the expression amount of CARP gene.

The constituents of determination kit IV are the same as those of determination kit I except medium (ii).

Determination kit IV enables the easy determination of susceptibility to CARP target drug. Hence, determination method IV is useful for, for example, the evaluation of an action of CARP target drug on a particular animal and the like.

8.2. Determination Methods and Determination Kits for Susceptibility to CARP Target Drug on the Basis of Measurement of Polymorphism of CARP Gene 8.2.1. Determination Method for Susceptibility to CARP Target Drug in Disease Associated with CARP Target Drug on the Basis of Measurement of Polymorphism of CARP Gene (Determination Method V)

The present invention provides a determination method for susceptibility to CARP target drug in a disease associated with CARP target drug, which comprises measuring the polymorphism of CARP gene.

This determination method is abbreviated to as "determination method V" as required.

In one embodiment, determination method V comprises the following steps (a) and (b):

(a) a step for measuring the polymorphism of CARP gene in a biological sample collected from an animal;
(b) a step for predicting the effect of CARP target drug in a disease associated with CARP gene on the basis of the presence or absence of a particular type of polymorphism.

The methodology comprising the above-described steps (a) and (b) is abbreviated to as "methodology VIII" as required.

Step (a) of methodology VIII is the same as step (a) of methodology VII.

In step (b) of methodology VIII, the effect of CARP target drug in a disease associated with CARP target drug is evaluated on the basis of the type of polymorphism of CARP gene. Specifically, first, the measured type of polymorphism of CARP gene is checked against data on the correlation between the type of polymorphism of CARP gene and susceptibility to CARP target drug in a disease associated with CARP target drug. This correlation can be determined by a method known per se.

Next, from the result of the checking, susceptibility to CARP target drug in a disease associated with CARP target drug is estimated. It is known that in animals that are highly susceptible to a drug, a particular type of polymorphism is often observed in the CARP gene. Hence, it is possible to determine the susceptibility of an animal to CARP target drug by analyzing polymorphism. For example, provided that CARP target drug is a drug, the likelihood or unlikelihood of obtainment of desired effect of the drug, or the probability of onset of adverse reaction of a drug, can be determined.

Determination method V enables the easy determination of susceptibility to CARP target drug in a disease associated with CARP target drug (e.g., allergic diseases, a disease for which regulation of release of a chemical mediator is desired). Hence, determination method V is useful for, for example, the evaluation of an action of CARP target drug in a disease associated with CARP target drug and the like.

8.2.2. Determination Kit for Susceptibility to CARP Target Drug in Disease Associated with CARP Target Drug on the Basis of Measurement of Polymorphism of CARP Gene (Determination Kit V)

The present invention also provides a determination kit that enables the easy conduct of determination method V.

This determination kit is abbreviated to as "determination kit V" as required.

In one embodiment, determination kit V comprises the following (i) and (ii):
(i) a means enabling a measurement of the polymorphism of CARP gene;
(ii) a medium recording the relationship between the effect of CARP target drug and the polymorphism of CARP gene.

The constituents of determination kit V are the same as those of determination kit II except medium (ii).

Determination kit V enables a determination of susceptibility to CARP target drug in a disease associated with CARP target drug (e.g., allergic diseases, a disease for which regulate of release of a chemical mediator is desired). Hence, determination kit V is useful for, for example, the evaluation of an action of CARP target drug in a disease associated with CARP target drug and the like.

8.2.3. Determination Method for Susceptibility to CARP Target Drug in Disease Associated with CARP Gene on the Basis of Measurement of Polymorphism of CARP Gene (Determination Method VI)

The present invention provides a determination method for susceptibility to CARP target drug in a disease associated with CARP gene, which comprises measuring the polymorphism of CARP gene.

This determination method is abbreviated to as "determination method VI" as required.

In one embodiment, determination method VI comprises the following steps (a) and (b):
(a) a step for measuring the type of polymorphism of CARP gene in a biological sample collected from an animal;
(b) a step for predicting the effect of CARP target drug in a disease associated with CARP gene on the basis of the presence or absence of a particular type of polymorphism.

In this determination method, the type of polymorphism used to determine the susceptibility is one that alters the ability of CARP to bind to CARP target drug. The type of polymorphism can be determined by a method known per se such as binding assay. Animals having a target gene comprising the type of polymorphism that potentiates or reduces the binding ability to the drug are thought to be highly (or poorly) susceptible to the drug; animals having a target gene comprising a type of polymorphism that reduces the binding ability are considered to be less (or more) susceptible. Hence, the susceptibility of an animal to CARP target drug can be determined by analyzing the type of polymorphism.

The methodology comprising steps (a) and (b) above in determination method VI is the same as methodology VIII except for the type of polymorphism of CARP gene to be measured.

Determination method VI enables the easy determination of susceptibility to CARP target drug in a disease associated with CARP target drug. Hence, determination method VI is useful for, for example, the evaluation of an action of CARP target drug in a disease associated with CARP target drug and the like.

8.2.4. Determination Kit for Susceptibility to CARP Target Drug in Disease Associated with CARP Gene on the Basis of Measurement of Polymorphism of CARP Gene (Determination Kit VI)

The present invention also provides a determination kit that enables the easy conduct of determination method VI.

This determination kit is abbreviated to as "determination kit VI" as required.

In one embodiment, determination kit VI comprises the following (i) and (ii):
(i) a means enabling a measurement of the polymorphism of CARP gene;
(ii) a medium recording the relationship between a disease associated with CARP gene and the polymorphism of CARP gene.

In determination kit VI, the type of polymorphism used to determine the risk of onset is one that alters the ability of CARP to bind to CARP target drug. The type of polymorphism can be determined by a method known per se such as binding assay.

The constituents of determination kit VI are the same as those of determination kit V except for the type of polymorphism of CARP gene to be measured.

Determination kit VI enables a determination of susceptibility to CARP target drug in a disease associated with CARP target drug. Hence, determination kit VI is useful for, for example, the evaluation of an action of CARP target drug in a disease associated with CARP target drug and the like.

The disclosures in all publications mentioned herein, including patents and patent application specifications, are incorporated by reference herein to the extent that all of them have been given expressly.

EXAMPLES

The present invention is hereinafter described in more detail by means of the following examples, which, however, are not to be construed as limiting the present invention.

Reference Example 1

Method of Expressing Proteins from Human Full-Length cDNA Clone

BP-reaction was performed on human full-length cDNA clone and the cloning vector Gateway pDONR201 by the PCR cloning method using the Invitrogen Gateway system to yield an entry clone. LR-reaction was performed on this entry clone with the destination vector pDEST17 (Gateway System) and LR Clonase at 25° C. for 60 minutes to yield an expression plasmid. *Escherichia coli* competent cell BL21star(DE3)pLysS were transformed with this expression plasmid, a clone incorporating the expression vector was selected, and a frozen stock was prepared. The transformant was inoculated into LB medium and precultured, after which it was transferred into SB medium and cultured to induce the expression by IPTG, and the cells were stored frozen.

Reference Example 2

Method of Purifying the Expressed Protein of Human Full-Length cDNA Clone

A human full-length cDNA clone was expressed as a protein with an N-terminal His tag. This clone was purified using BioRobot 8000 (Qiagen) or ACTA Crystal (Amersham). In the purification with BioRobot 8000, the expression-induced frozen stock cells in Reference Example 1 was thawed and lysed with lysozyme, after which the cells were affinity-purified using Ni-NTA Superflow 96 BioRobot Kit (Qiagen). In the purification with ACTA Crystal, affinity purification using a HisTrap HP column was followed by gel filtration purification using the Gel Filtration Column HiLoad 16/60 or a 10/30 Superdex 75 prep grade column. The purified fraction was used for interaction analysis after being subjected to SDS-PAGE to verify the estimated molecular weight and purity.

Reference Example 3

Figure 2:
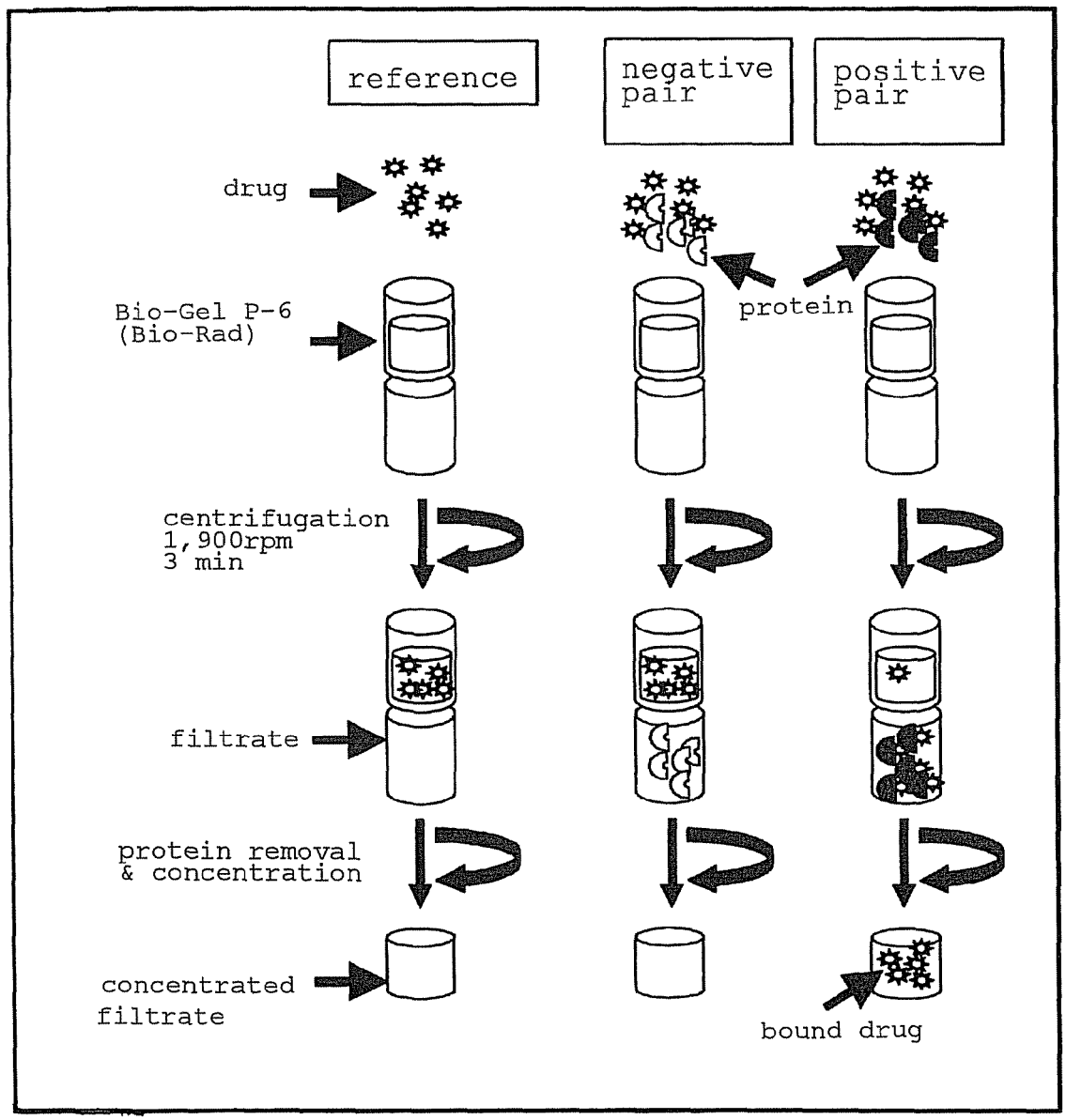
FIG. 2 shows a schematic diagram showing a SEC interaction analysis using a spin column.

Method of Analyzing Human Protein-Drug Interactions Using Size Exclusion Chromatography To analyze the interactions between commonly used drugs and proteins expressed from human full-length cDNA clones while keeping both the proteins and the compounds in non-modified, non-immobilized state, size exclusion chromatography (SEC) and mass analysis were used in combination (FIGS. 1 and 2). The specific procedures are shown below.
Step 1
A solution of a single drug or a multiplexed compound solution comprising a mixture of a plurality of drugs (e.g., 8 kinds, 16 kinds, 24 kinds) was added to the protein purified in Reference Example 2.
Step 2
The compound-protein mixture prepared in step 1 was subjected to chromatography using an SEC column, the compound and the protein were separated by SEC, and the bound compound or compound that interacted with the protein in the protein fraction was analyzed using a mass analyzer.
The purified protein standard was concentrated by To ultrafiltration and subjected to buffer solution exchange, and finally concentrated to obtain a concentration of 25 μM or higher in an aqueous solution of 10 mM ADA (N-(2-acetamido)iminodiacetic acid) buffer (pH 6.5)-300 mM NaCl-100 μM mineral ion cocktail, $Ca(OAc)_2$, $Zn(OAc)_2.2H_2O$, $Cu(OAc)_2.H_2O$, $Co(OAc)_2.4H_2O$, $Mn(OAc)_2.4H_2O$, $Mg(OAc)_2.4H_2O$, $FeCl_3.6H_2O$). Protein concentrations were measured using BCA Protein Assay (PIERCE), in consideration of the purity calculated by SDS-PAGE.

A solution of a single pharmaceutical compound at a concentration of 1.25 mM in DMSO (dimethyl sulfoxide) or a multiplexed compound solution of a plurality (8 or 16 kinds) of compounds in DMSO was prepared, and these solutions were used for interaction analysis. In reproducibility confirmation experiments or concentration-dependent determination experiments, a solution of various concentrations of a single compound in DMSO (dimethyl sulfoxide) was used.

Mass analysis was performed using LCQ DECA XP (Thermoelectron) or Q-TOFmicro (Micromass), equipped with an ESI probe. The LC pump used was Agilent 1100 (Yokogawa Analytical Systems), and the autosampler used was HTC-PAL (CTC Analytics) equipped with a cooling stacker.

In the SEC method using a 384-well spin column, Unifilter 100 (Whatman), packed with 10 μL (dry volume) of Bio-Gel P6 (BIO-RAD) and swollen with milliQ water, was used as the SEC column. 13.3 μL of a protein-free reference standard or a 25 μM protein standard and 0.7 μL of a multiplexed liquid comprising 25 μM of each pharmaceutical compound (5% DMSO aqueous solution) were mixed; 9 μL of this mixture was aliquoted into the SEC spin columns. The SEC spin column was mounted on an acetonitrile-aliquoted 384-well U-bottom plate and centrifuged; the SEC spin column filtrate, which is a protein fraction, was retrieved in 50% acetonitrile. The protein precipitate produced by the acetonitrile was removed via centrifugation and filtration for protein removal; the resulting filtrate was concentrated by centrifugation and re-dissolved in 10 μL of 50% methanol to obtain a mass analysis sample. The mobile phase supplied to the mass analyzer was 0.1% formic acid/50% methanol solution in the positive ion mode, and 0.1% ammonia/50% methanol solution in the negative ion mode; these mobile phases were used at a flow rate of 40 μL/min. 2-μL of mass analysis samples were injected using an autosampler at 2-Minute intervals; the mass spectral intensity of the compound was measured to obtain the spectral intensity of the pharmaceutical compound contained in the SEC spin column filtrate (protein fraction eluted from SEC). The protein and the compound were judged to have interacted with each other if the spectral intensity of the compound in a mass analysis sample obtained from an SEC sample supplemented with a protein standard was greater than the spectral intensity of the compound in a mass analysis sample of reference SEC standard not supplemented with the protein. In the experiments for examining concentration dependency, the protein and the compound were judged to have interacted with each other concentration-dependently if the spectral intensity of the pharmaceutical compound contained in the SEC spin column filtrate (protein fraction eluted from SEC) increased as the compound concentration or/and protein concentration of the SEC sample was increased.

Example 1

Analysis of interaction between FLJ13397-derived protein and astemizole or terfenadine The FLJ13397 clone-derived protein (CARP) was expressed and purified according to the methods of Reference Examples 1 and 2, and the interaction between the protein expressed and purified from FLJ13397 and astemizole or terfenadine was analyzed according to the method of Reference Example 3. The results (spectrum intensity of the extracted mass range) are shown in Tables 1 and 2. The spectrum intensity of the pharmaceutical compound contained in the SEC spin column filtrate (protein fraction eluted from SEC) increased depending on the doses of both the small compound and the FLJ13397-expressed protein, respectively, from which we determined that to there was a concentration-dependent interaction.

TABLE 1

| | | Measured Mass Range: m/z = 472.0-473.0 | | | | |
|---|---|---|---|---|---|---|
| FLJ13397-Terfenadine | | compound (μM) | | | | |
| | | 0 | 1 | 10 | 100 | 250 |
| protein (μM) | 0 | 2637565 | 1817431 | 2641416 | 241452949 | 644365611 |
| | 23.75 | 1199490 | 1889743 | 9434699 | 175843248 | 1389061661 |
| | 47.5 | 1381695 | 1281933 | 8393491 | 549040113 | 1700398168 |

TABLE 2

| Measured Mass Range: m/z = 458.9-459.9 | | | | | |
|---|---|---|---|---|---|
| FLJ13397-Astemizole | compound (μM) | | | | |
| | 0 | 1 | 10 | 100 | 250 |
| protein (μM)  0 | 33202385 | 12239048 | 13557249 | 210085727 | 710392964 |
| 23.75 | 16126281 | 16006165 | 118520633 | 1213216132 | 1027353172 |
| 47.5 | 12920683 | 18099237 | 36678174 | 2237504347 | 2019252410 |

Hence, the FLJ13397-derived protein was found to be a target protein for astemizole or terfenadine, which is a compound developed as an antiallergic drug. Therefore, a new antiallergic drug can be screened by making the FLJ13397-derived protein interact with screening candidate substances. Specifically, a new antiallergic drug can be screened by, for example, constructing a system which detects the interaction between the FLJ13397-derived protein and a candidate substance according to the method of Example 1.

Example 2
Analysis of Interaction Between FLJ13397 Clone-Derived Protein and Various Compounds The FLJ13397 clone-derived protein was expressed and purified according to the methods of Reference Examples 1 and 2, and the interaction between the protein expressed and purified from FLJ13397 and various compounds was analyzed according to the method of Reference Example 3. The results are shown in Tables 3-20. The spectrum intensity of the pharmaceutical compound contained in the SEC spin column filtrate (protein fraction eluted from SEC) increased, depending on the doses of both the various compounds and the FLJ13397-expressed protein, from which we determined that there was a concentration-dependent interaction between them.

TABLE 3

| Measured Mass Range: m/z = 613.0-614.0 | | | | | |
|---|---|---|---|---|---|
| FLJ13397-Lasalocid sodium salt | compound (μM) | | | | |
| | 0 | 1 | 10 | 100 | 250 |
| protein (μM)  0 | 18324138 | 9674294 | 13154726 | 945932706 | 2174989976 |
| 23.75 | 13302470 | 11601595 | 20062681 | 2538387120 | 9287976762 |
| 47.5 | 9229391 | 10467838 | 46504126 | 3226817361 | 9802098210 |

TABLE 4

| Measured Mass Range: m/z = 267.7-268.7 | | | | | |
|---|---|---|---|---|---|
| FLJ13397-α,α-Diphenyl-4-piperidino-methanol (Alpha,alpha-Diphenyl-4-piperidino-methanol) | compound (μM) | | | | |
| | 0 | 1 | 10 | 100 | 250 |
| protein (μM)  0 | 1051183 | 1354498 | 14109120 | 106849236 | 400374746 |
| 23.75 | 851381 | 1217276 | 12131847 | 219345185 | 620399620 |
| 47.5 | 873213 | 1961004 | 15743409 | 287013305 | 1037919 |

TABLE 5

| Measured Mass Range: m/z = 374.8-375.8 | | | | | |
|---|---|---|---|---|---|
| FLJ13397-Hydroxyzine | compound (μM) | | | | |
| | 0 | 1 | 10 | 100 | 250 |
| protein (μM)  0 | 91915895 | 112855827 | 134387910 | 300477422 | 922692583 |
| 23.75 | 112630229 | 126033923 | 108540593 | 567712336 | 919366054 |
| 47.5 | 110593131 | 89527484 | 115214088 | 554713461 | 1073610880 |

TABLE 6

Measured Mass Range: m/z = 444.8-445.8

| FLJ13397-Desmethyl-astemizole | | compound (μM) | | | |
|---|---|---|---|---|---|
| | 0 | 1 | 10 | 100 | 250 |
| protein (μM) 0 | 12753644 | 12076364 | 6489161 | 85510154 | 135192715 |
| 23.75 | 10368906 | 10091649 | 12628724 | 141884756 | 339921213 |
| 47.5 | 10638211 | 10876345 | 26276867 | 225675004 | 728918987 |

TABLE 7

Measured Mass Range: m/z = 223.7-224.7

| FLJ13397-2-Amino-1-Benzyl-benzimidazole | | compound (μM) | | | |
|---|---|---|---|---|---|
| | 0 | 1 | 10 | 100 | 250 |
| protein (μM) 0 | 4162174 | 5598524 | 4341825 | 12703620 | 39100216 |
| 23.75 | 2833206 | 1659600 | 4509110 | 32945929 | 125775631 |
| 47.5 | 4304643 | 2958392 | 7550402 | 42993061 | 559844 |

TABLE 8

Measured Mass Range: m/z = 191.7-192.7

| FLJ13397-Carbendazim | | compound (μM) | | | |
|---|---|---|---|---|---|
| | 0 | 1 | 10 | 100 | 250 |
| protein (μM) 0 | 7898834 | 20852664 | 22203544 | 20562919 | 34177767 |
| 23.75 | 15308057 | 16443963 | 21673683 | 35342827 | 129995989 |
| 47.5 | 24351353 | 24660680 | 32996198 | 65044479 | 148437211 |

TABLE 9

Measured Mass Range: m/z = 249.7-250.7

| FLJ13397-Oxibendazole | | compound (μM) | | | |
|---|---|---|---|---|---|
| | 0 | 1 | 10 | 100 | 250 |
| protein (μM) 0 | 921022 | 570160 | 525337 | 1292692 | 2449247 |
| 23.75 | 485333 | 595458 | 3533115 | 7303166 | 20401030 |
| 47.5 | 330688 | 529117 | 9671167 | 8921904 | 13559202 |

TABLE 10

Measured Mass Range: m/z = 265.9-266.9

| FLJ13397-Albendazole | | compound (μM) | | | |
|---|---|---|---|---|---|
| | 0 | 1 | 10 | 100 | 250 |
| protein (μM) 0 | 205110 | 99130 | 25263 | 221630 | 151791 |
| 23.75 | 317187 | 290428 | 1117765 | 6713076 | 18185332 |
| 47.5 | 143406 | 247973 | 603904 | 3946588 | 55508710 |

TABLE 11

Measured Mass Range: m/z = 281.7-282.7

| FLJ13397-Albendazole Sulfoxide | | compound (μM) | | | |
|---|---|---|---|---|---|
| | 0 | 1 | 10 | 100 | 250 |
| protein (μM) 0 | 1631276 | 1514429 | 11869270 | 125971079 | 460535649 |
| 23.75 | 1048768 | 1280086 | 13449119 | 208777846 | 532900104 |
| 47.5 | 1013026 | 1361540 | 14241157 | 241218904 | 372564422 |

TABLE 12

Measured Mass Range: m/z = 297.9-298.9

| FLJ13397-Albendazole Sulfone | | compound (μM) | | | | |
|---|---|---|---|---|---|---|
| | | 0 | 1 | 10 | 100 | 250 |
| protein (μM) | 0 | 947123 | 1342766 | 5960539 | 94575228 | 66281031 |
| | 23.75 | 725508 | 1155288 | 5481616 | 149841728 | 280956724 |
| | 47.5 | 1107557 | 761260 | 5089101 | 131428354 | 328407687 |

TABLE 13

Measured Mass Range: m/z = 239.8-240.8

| FLJ13397-2-Amino-5-N-Propyl-sulphonyl-benzimidazole | | compound (μM) | | | | |
|---|---|---|---|---|---|---|
| | | 0 | 1 | 10 | 100 | 250 |
| protein (μM) | 0 | 1266664 | 825049 | 1750199 | 36160236 | 91113992 |
| | 23.75 | 344207 | 360734 | 1437041 | 53411123 | 98334673 |
| | 47.5 | 403491 | 484482 | 1664928 | 52719227 | 159174682 |

TABLE 14

Measured Mass Range: m/z = 296.0-297.0

| FLJ13397-Mebendazole | | compound (μM) | | | | |
|---|---|---|---|---|---|---|
| | | 0 | 1 | 10 | 100 | 250 |
| protein (μM) | 0 | 621163 | 495347 | 525296 | 482901 | 444136 |
| | 23.75 | 344961 | 480780 | 777305 | 15054045 | 32097734 |
| | 47.5 | 437886 | 495499 | 725295 | 9517765 | 43484997 |

TABLE 15

Measured Mass Range: m/z = 301.7-302.7

| FLJ13397-Nocodazole | | compound (μM) | | | | |
|---|---|---|---|---|---|---|
| | | 0 | 1 | 10 | 100 | 250 |
| protein (μM) | 0 | 6148411 | 8235638 | 4879694 | 6162151 | 9512433 |
| | 23.75 | 4661853 | 5202611 | 6159010 | 33749400 | 131043824 |
| | 47.5 | 4356636 | 3977550 | 9316181 | 37180973 | 227971112 |

TABLE 16

Measured Mass Range: m/z = 315.8-316.8

| FLJ13397-Oxfendazole | | compound (μM) | | | | |
|---|---|---|---|---|---|---|
| | | 0 | 1 | 10 | 100 | 250 |
| protein (μM) | 0 | 15686675 | 23723676 | 28662280 | 106348780 | 128622627 |
| | 23.75 | 28292077 | 29471243 | 41004899 | 160312456 | 264420112 |
| | 47.5 | 26306586 | 35025210 | 42911925 | 180803127 | 506800735 |

TABLE 17

Measured Mass Range: m/z = 331.8-332.8

| FLJ13397-Fenbendazole Sulfone | | compound (μM) | | | | |
|---|---|---|---|---|---|---|
| | | 0 | 1 | 10 | 100 | 250 |
| protein (μM) | 0 | 3139151 | 4524987 | 9471873 | 4055561 | 5180253 |
| | 23.75 | 2516140 | 2681468 | 13569838 | 63176239 | 165761033 |
| | 47.5 | 2493489 | 2967134 | 12568548 | 88590858 | 286102392 |

TABLE 18

Measured Mass Range: m/z = 133.8-134.8

| FLJ13397-2-Aminobenzimidazole | | compound (μM) | | | | |
|---|---|---|---|---|---|---|
| | | 0 | 1 | 10 | 100 | 250 |
| protein (μM) | 0 | 207196 | 276565 | 153479 | 437739 | 2837732 |
| | 23.75 | 59867 | 42562 | 69826 | 1819414 | 7370524 |
| | 47.5 | 25382 | 152781 | 71963 | 2080493 | 8155388 |

TABLE 19

Measured Mass Range: m/z = 201.8-202.8

| FLJ13397-Thiabendazole | | compound (μM) | | | | |
|---|---|---|---|---|---|---|
| | | 0 | 1 | 10 | 100 | 250 |
| protein (μM) | 0 | 62372047 | 61442947 | 21903023 | 60344905 | 40530147 |
| | 23.75 | 61754446 | 42216896 | 45510612 | 64811390 | 93902905 |
| | 47.5 | 51620355 | 47595391 | 41434122 | 63585895 | 125101370 |

TABLE 20

Measured Mass Range: m/z = 118.7-119.7

| FLJ13397-Benzimidazole | | compound (μM) | | | | |
|---|---|---|---|---|---|---|
| | | 0 | 1 | 10 | 100 | 250 |
| protein (μM) | 0 | 3447058 | 2459590 | 2937731 | 3881633 | 9545633 |
| | 23.75 | 2236733 | 1627696 | 1321952 | 4636579 | 10439034 |
| | 47.5 | 2437878 | 1328076 | 2620286 | 4337586 | 13446649 |

Hence, the FLJ13397-derived protein was found to be a target protein for these various compounds. Therefore, a new drug can be screened by making the FLJ13397-derived protein interact with screening candidate substances. Specifically, a new drug can be screened by, for example, constructing a system which detects the interaction between the FLJ13397-derived protein and a candidate substance according to the method of Example 1.

INDUSTRIAL APPLICABILITY

The CARP and genes of the present invention enable the development of antiallergic drugs and the like. The screening methods of the present invention and the derivative production method of the present invention enable the development of prophylactic or therapeutic agents for diseases such as allergic diseases and the like, and investigational reagents for the diseases, and the like. The regulators and derivatives of the present invention can be used for the prophylaxis or treatment of diseases such as allergic diseases and the like, and investigational reagents for the diseases and the like. The complexes and kits of the present invention can be used for the screening methods of the present invention and the like. The determination methods and determination kits of the present invention enable the evaluation of the onset or likelihood of onset of diseases in animals, and the evaluation of the susceptibility of animals to drugs and the like.

This application is based on patent application Nos. 2004-303432 (filing date: Oct. 18, 2004) and 2005-089609 (filing date: Mar. 25, 2005) filed in Japan, the contents of which are incorporated in full herein by this reference.

The invention claimed is:

1. A screening method comprising determining whether or not a test substance regulates the expression or function of a nucleic acid encoding caspase recruitment domain containing protein (CARP), wherein the test substance is a substance that regulates allergic symptoms, a substance that regulates the release of a chemical mediator, or a substance that regulates arrhythmic symptoms, which comprises the following steps (a)-(c):
   (a) a step for bringing the test substance in contact with (i) CARP or (ii) a mutant protein thereof that consists of the amino acid sequence of SEQ ID NO: 2, wherein 1-30 amino acids have been deleted, substituted, added, or inserted;
   (b) a step for measuring the functional level of CARP or the mutant protein thereof in the presence of the test substance, and comparing the functional level with that of CARP or the mutant protein thereof in the absence of the test substance;
   (c) a step for selecting a test substance that alters the functional level of CARP or the mutant protein thereof on the basis of the results of the comparison in step (b) above.

2. A screening method comprising determining whether or not a test substance regulates the expression or function of a nucleic acid encoding caspase recruitment domain containing protein (CARP), wherein the test substance is a substance that regulates allergic symptoms, a substance that regulates the release of a chemical mediator, or a substance that regulates arrhythmic symptoms, which comprises the following steps (a), (b) and (c):
   (a) a step for bringing the test substance and a CARP-binding substance into contact with (i) CARP or (ii) a mutant protein thereof that consists of the amino acid sequence of SEQ ID NO: 2, wherein 1-30 amino acids have been deleted, substituted, added, or inserted;
   (b) a step for measuring the binding level of the binding substance to CARP or the mutant protein thereof in the presence of the test substance, and comparing this binding level with the binding level of the binding substance to CARP or the mutant protein thereof in the absence of the test substance;
   (c) a step for selecting a test substance that alters the binding level of the binding substance to CARP or the mutant protein thereof on the basis of the results of the comparison in step (b) above.

3. The method according to claim 2, wherein the CARP-binding substance is astemizole or terfenadine, or metabolite thereof, or α, α-diphenyl-4-pipefidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonyl-benzimidazole, mebendazole, nocodazol, oxfendazole, fenbendazole sulfone, 2-aminobenzimidazole, thiabendazole, benzimidazole or lasalocid, or a derivative thereof capable of binding to CARP.

4. A screening method for a substance capable of regulating a function associated with a nucleic acid encoding caspase recruitment domain containing protein (CARP), which comprises determining whether or not a test substance is capable of regulating the binding ability of a CARP target drug to (i) CARP or (ii) a mutant protein thereof that consists of the amino acid sequence of SEQ ID NO: 2, wherein 1-30 amino acids have been deleted, substituted, added, or inserted, which comprises the following steps (a) to (c):
   (a) a step for bringing the test substance and the CARP target drug into contact with (i) CARP or (ii) a mutant protein thereof that consists of the amino acid sequence of SEQ ID NO: 2, wherein 1-30 amino acids have been deleted, substituted, added, or inserted;
   (b) a step for measuring the binding level of the CARP target drug to CARP or the mutant protein thereof in the presence of the test substance, and comparing this binding level with the binding level of the CARP target drug to CARP or the mutant protein thereof in the absence of the test substance;
   (c) a step for selecting a test substance that alters the binding level of the CARP target drug to CARP or the mutant protein thereof on the basis of the results of the comparison in step (b) above.

5. The method according to claim 4, wherein the CARP target drug is astemizole or terfenadine, or metabolite thereof, or α, α-diphenyl-4-piperidinomethanol, hydroxyzine, desmethylastemizole, 2-amino-1-benzylbenzimidazole, carbendazim, oxibendazole, albendazole, albendazole sulfoxide, albendazol sulfone, 2-amino-5-N-propylsulfonylbenzimidazole, mebendazole, nocodazol, oxfendazole, fenbendazole sulfone, 2-aminobenzimidazole, thiabendazole, benzimidazole or lasalocid, or a derivative thereof capable of binding to CARP.

6. The method of claim 1, wherein the mutant protein consists of the amino acid sequence of SEQ ID NO: 2, wherein 1-20 amino acids have been deleted, substituted, added, or inserted.

7. The method of claim 2, wherein the mutant protein consists of the amino acid sequence of SEQ ID NO: 2, wherein 1-20 amino acids have been deleted, substituted, added, or inserted.

8. The method of claim 4, wherein the mutant protein consists of the amino acid sequence of SEQ ID NO: 2, wherein 1-20 amino acids have been deleted, substituted, added, or inserted.

* * * * *

UNITED STATES PATENT AND TRADEMARK OFFICE
CERTIFICATE OF CORRECTION

PATENT NO. : 8,153,385 B2
APPLICATION NO. : 11/577350
DATED : April 10, 2012
INVENTOR(S) : Yamauchi et al.

It is certified that error appears in the above-identified patent and that said Letters Patent is hereby corrected as shown below:

In the claims:

In column 64, claim 3, line 34, "α-diphenyl-4-pipefidinomethanol" should read "α-diphenyl-4-piperidinomethanol"

Signed and Sealed this
Seventh Day of August, 2012

David J. Kappos
*Director of the United States Patent and Trademark Office*